United States Patent
Ainley et al.

(10) Patent No.: US 10,415,046 B2
(45) Date of Patent: Sep. 17, 2019

(54) PRECISION GENE TARGETING TO A PARTICULAR LOCUS IN MAIZE

(71) Applicant: DOW AGROSCIENCES LLC, Indianapolis, IN (US)

(72) Inventors: W. Michael Ainley, Carmel, IN (US); James W. Bing, Zionsville, IN (US); David R. Corbin, Carmel, IN (US); Steven L. Evans, Zionsville, IN (US); Joseph F. Petolino, Zionsville, IN (US); Lakshmi Sastry-Dent, Avon, IN (US); Steven A. Thompson, Carmel, IN (US); Steven R. Webb, Westfield, IN (US); Mary E. Welter, Westfield, IN (US); Ning Zhou, Zionsville, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 138 days.

(21) Appl. No.: 15/338,888

(22) Filed: Oct. 31, 2016

(65) Prior Publication Data
US 2017/0044558 A1   Feb. 16, 2017

Related U.S. Application Data

(63) Continuation of application No. 14/105,563, filed on Dec. 13, 2013, now abandoned.

(60) Provisional application No. 61/820,231, filed on May 7, 2013, provisional application No. 61/736,856, filed on Dec. 13, 2012.

(51) Int. Cl.
C12N 15/82 (2006.01)
C12N 9/12 (2006.01)

(52) U.S. Cl.
CPC ....... *C12N 15/8213* (2013.01); *C12N 9/1241* (2013.01); *C12Y 207/07047* (2013.01)

(58) Field of Classification Search
None
See application file for complete search history.

(56) References Cited

U.S. PATENT DOCUMENTS

| | | | |
|---|---|---|---|
| 5,356,802 A | 10/1994 | Chandrasegaran | |
| 5,420,032 A | 5/1995 | Marshall et al. | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,534,261 B1 | 3/2003 | Cox et al. | |
| 6,824,978 B1 | 11/2004 | Cox et al. | |
| 6,833,252 B1 | 12/2004 | Dujon et al. | |
| 6,933,113 B2 | 8/2005 | Case | |
| 8,273,535 B2 | 9/2012 | Song | |
| 2003/0232410 A1 | 12/2003 | Liljedahl et al. | |
| 2005/0026157 A1 | 2/2005 | Baltimore et al. | |
| 2005/0064474 A1 | 3/2005 | Umov et al. | |
| 2005/0208489 A1 | 9/2005 | Carroll et al. | |
| 2006/0188987 A1 | 8/2006 | Guschan et al. | |
| 2007/0117128 A1 | 5/2007 | Smith et al. | |
| 2007/0134796 A1 | 6/2007 | Holmes et al. | |
| 2008/0182332 A1 | 7/2008 | Cai et al. | |
| 2009/0093366 A1 | 4/2009 | Wright et al. | |
| 2009/0104700 A1 | 4/2009 | Samuel et al. | |
| 2009/0111119 A1 | 4/2009 | Doyon et al. | |
| 2009/0205083 A1* | 8/2009 | Gupta | C12N 15/8213 800/298 |
| 2009/0263900 A1 | 10/2009 | DeKelver et al. | |
| 2011/0129829 A1* | 6/2011 | Song | C12Q 1/6895 435/6.11 |

(Continued)

FOREIGN PATENT DOCUMENTS

| | | |
|---|---|---|
| GB | 2338237 | 12/1999 |
| WO | WO 95/19431 | 7/1995 |
| WO | WO 96/06166 | 2/1996 |

(Continued)

OTHER PUBLICATIONS

Akiyama et al (Interlaboratory Validation of an Event-Specific Real Time Polymerase Chain Reaction Detection Method for Genetically Modified DAS59132 Maize. J. Food Hyg. Soc. Japan vol. 51, No. 2: 65-70, Apr. 2010).*

Andersson et al (Response to the request from the European Commission on the non-authorised genetically modified event DAS 59132-8 in US maize. Scientific Opinion of the Panel on Genetically Modified Organisms. The EFSA Journal. 713, 1-10, 2008).*

Argast, et al., "I-PPOI and I-CREI Homing Site Sequence Degeneracy Determined by Random Mutagenesis and Sequential In Vitro Enrichment," J. Mol. Biol. 280:345-353 (Jul. 1998).

(Continued)

*Primary Examiner* — Medina A Ibrahim
*Assistant Examiner* — Wayne Zhong

(57) ABSTRACT

The present invention claims methods for the stable integration of exogenous DNA into a specific locus, E32, in the maize genome through the use of zinc finger nucleases. Maize plants and plant parts that were transformed by the methods of the invention are claimed. The invention is useful for creating desirable traits such as herbicide resistance, herbicide tolerance, insect resistance, insect tolerance, disease resistance, disease tolerance, stress tolerance, and stress resistance in maize The E32 locus represents a superior site for inserting foreign genes because native agronomic phenotypes are not disturbed.

13 Claims, 8 Drawing Sheets
Specification includes a Sequence Listing.

(56) References Cited

U.S. PATENT DOCUMENTS

2013/0326645 A1* 12/2013 Cost .................. C12N 15/85
800/14

FOREIGN PATENT DOCUMENTS

| WO | WO 98/37186 | 8/1998 | | |
|----|----|----|----|----|
| WO | WO 98/53057 | 11/1998 | | |
| WO | WO 98/53058 | 11/1998 | | |
| WO | WO 98/53059 | 11/1998 | | |
| WO | WO 98/53060 | 11/1998 | | |
| WO | WO 98/54311 | 12/1998 | | |
| WO | WO 00/27878 | 5/2000 | | |
| WO | WO 01/53480 | 7/2001 | | |
| WO | WO 01/60970 | 8/2001 | | |
| WO | WO 01/88197 | 11/2001 | | |
| WO | WO 02/016536 | 2/2002 | | |
| WO | WO 02/077227 | 10/2002 | | |
| WO | WO 02/099084 | 12/2002 | | |
| WO | WO 03/016496 | 2/2003 | | |
| WO | WO 05/084190 | 9/2005 | | |
| WO | WO 06/071219 | 7/2006 | | |
| WO | WO 06/097854 | 9/2006 | | |
| WO | WO 07/014275 | 1/2007 | | |
| WO | WO 07/139898 | 12/2007 | | |
| WO | WO 08/133938 | 11/2008 | | |
| WO | WO 2009/100188 | 8/2009 | | |
| WO | WO 2010/077319 | 7/2010 | | |
| WO | WO 2013026740 | 2/2013 | | |
| WO | WO-2013026740 A2 * | 2/2013 | .......... | C12N 9/0069 |
| WO | WO 2013/169802 | 11/2013 | | |

OTHER PUBLICATIONS

Armstrong, et al., "Development and Availability of Germplasm With High Type II Culture Formation," Maize Genet Coop News Lett 65:92-93 (1991).
Ashworth, et al., "Computational Redesign of Endonuclease DNA Binding and Cleavage Specificity," Nature 441:656-659 (Jun. 2006).
Belfort, et al., "Homing Endonucleases: Keeping the House in Order," Nucleic Acids Research 25:33793388 (accepted Jul. 1997).
Bibikova, et al., "Stimulation of Homologous Recombination Through Targeted Cleavage by Chimeric Nucleases," Mol. Cell. Biol. 21:289-297 (Jan. 2001).
Bitinate, et al., "Foki Dimerization Is Required for DNA Cleavage," PNAS USA 95:10570-10575 (Sep. 1998).
Boch, et al., "Breaking the Code of DNA Binding Specificity of TAL-Type III Effectors," Science 326:1509-1512 (Dec. 2009).
Chang, et al., "Modification of DNA Ends Can Decrease End Joining Relative to Homologous Recombination in Mammalian Cells," PNAS USA 84:4959-4963 (Jul. 1987).
Chevalier, et al., "Design, Activity, and Structure of a Highly Specific Artificial Endonuclease," Molecular Cell. 10:895-905(Oct. 2002).
Christensen, et al., "Maize Polyubiquitin Genes: Structure, Thermal Perturbation of Expression and Transcript Slicing, and Promotoer Activity Following Transfer to Protoplasts by Electroportation," Plant Mol Biol. 18(4):675-689 (Feb. 1992).
D'Halluin, et al., "Homologous Recombination: A Basis for Targeted Genome Optimization in Crop Species Such as Maize," Plant Biotechnology J. 6(1):93-102 (Jan. 2008).
Doyon, et al., "Heritable Targeted Gene Disruption in Zebrafish Using Designed Zinc-Finger Nucleases," Nature Biotechnology 26:702-708 (Jun. 2008).
Dujon, et al., "Mobile Introns: Definition of Terms and Recommended Nomenclature," Gene 82:115-118 (Oct. 1989).
Epinat, et al., "A Novel Engineered Meganuclease Induces Homologous Recombination in Yeast and Mammalian Cells," Nucleic Acids Research 31:2952-2962 (accepted Mar. 2003).
Frame, et al., "Agrobacterium Tumefaciens-Mediated Transformation of Maize Embryos Using a Standard Binary Vector System," Plant Physiol. 129:13-22 (May 2002).
Gimble, et al., "Substrate Recognition and Induced DNA Distortion by the PI-SCEI Endonuclease, An Enzvme Generated by Protein Splicing," J. Mol. Biol. 263:163-180 (Oct. 1996).
Gordon-Kamm, et al., "Transformation of Maize Cells and Regeneration of Fertile Transgenic Plants," Plant Cell 2:603-618 (Jul. 1990).
Iida, et al., "Modification of Endogenous Natural Genes by Gene Targeting in Rice and Other Higher Plants," Plant Mol. Biol. 59:205-219 (Sep. 2005).
Jasin, et al., "Genetic Manipulation of Genomes With Rare-Cutting Endonucleases," Trends Genet 12:224-228 (Jun. 1996).
Kim, et al., "Chimeric Restriction Endonuclease," PNAS USA. 91:883-887 (Feb. 1994).
Kim, et al., "Insertion and Deletion Mutants of FOKI Restriction Endonuclease," J. Biol. Chem. 269:31978-31982 (Dec. 1994).
Kim, et al., "Hybrid Restriction Enzymes: Zinc Finger Fusions to FOK I Cleavage Domain," Proc. Natl Acad. Sci. USA 93:1156-1160 (Feb. 1996).
Lawrence, et al., "Maizegdb, The Community Database for Maize Genetics and Genomics," Nucleic Acids Research 32:393-397 (accepted Aug. 27, 2003; published 2004).
Li, et al., "Functional Domains in FOK I Restriction Endonuclease," PNAS USA 89:4275-4279 (May 1992).
Li, et al., "Alteration of the Cleavage Distance of FOK I Restriction Endonuclease by Insertion Mutagenesis," PNAS USA 90:2764-2768 (Apr. 1993).
Lloyd, A. et al., "Targeted Mutagenesis Using Zinc-Finger Nucleases in *Arabidopsis*," Proc. Natl Acad. Sci. USA 102:2232-2237 (Feb. 2005).
Maeder, et al., "Rapid "Open-Source" Engineering of Customized Zincfinger Nucleases for Highly Efficient Gene Modification," Mol. Cell 31:294-301 (Jul. 2008).
McElroy, et al., "Isolation of an Efficient Actin Promotor for Use in Rice Transformation," The Plant Cell 2:163-171 (Feb. 1990).
Miller, et al., "Repetitive Zinc-Binding Domains in the Protein Transcription Factor IIIA From Xenopus Oocytes," EMBO J. 4:1609-1614 (received Apr. 4, 1985).
Miller, et al., "Rearrangement of Side-Chains in a ZIF268 Mutant Highlights the Complexities of Zinc Finger DNA Recognition," J Mol Biol., 313(2):309 (Oct. 2001).
Miller, et al., "An Improved Zinc-Finger Nuclease Architecture for Highly Specific Genome Editing," Nat Biotechnology 25:778-785 (Jul. 2007).
Moscou, et al., "A Simple Cipher Governs DNA Recognition by TAL Effectors," Science 326:1501 (Dec. 2009).
Nehls, et al., "Two Genetically Separable Steps in the Differentiation of Thymic Epithelium," Science 272:886-889 (May 1996).
Paques, et al., "Meganucleases and DNA Double-Strand Break-Induced Recombination: Perspectives for Gene Therapy," Current Gene Therapy 749-66 (Feb. 2007).
Perler, et al., "Protein Splicing Elements: Inteins and Exteins a Definition of Terms and Recommended Nomenclature," Nucleic Acids Research 22:1125-1127 (Apr. 1994).
Petolino, et al., "Whisker-Mediated Transformation of Embryogenic Callus of Maize," Plant Cell Rept. 12:781-786 (Jul. 2000).
Porteus, et al., "Chimeric Nucleases Stimulate Gene Targeting in Human Cells" Science 300:763 (May 2003).
Puchta, H.,"Gene Replacement by Homologous Recombination in Plants," Plant Mol. Biol. 48:173-182 (Jan. 2002).
Puchta, H., "The Repair of Double-Strand Breaks in Plants: Mechanisms and Consequences for Genome Evolution," J. Exp. Bot. 56:1-14 (published online Nov. 22, 2004).
Rhodes, et al., "Zinc Fingers: They Playa Key Part in Regulating the Activity of Genes in Many Species, From Yeast to Humans. Fewer Than 10 Years Ago No on Knew They Existed." Scientific American 268:56-65 (Feb. 1993).
Shukla, et al., "Precise Genome Modification in the Crop Species *Zea mays* Using Zinc-Finger Nucleases," Nature 459:437-441 (May 2009) with Supplementary on-line material.
Terada, et al., "Efficient Gene Targeting by Homologous Recombination in Rice," Nat Biotechnology 20: 1030-1034 (Sep. 2002).

(56) References Cited

OTHER PUBLICATIONS

Terada, et al., "Gene Targeting by Homologous Recombination as a Biotechnological Tool for Rice Functional Genomics," Plant Physiol 144:846-856 (Jun. 2007).
Tovkach, et al., "A Toolbox and Procedural Notes for Characterizing Novel Zinc Finger Nucleases for Genome Editing in Plant Cells," Plant J 57:747-757 (Feb. 2009).
Urnov, et al., "Highly Efficient Endogenous Human Gene Correction Using Designed Zincfinger Nucleases," Nature 435:646-651 (Jun. 2005).
Wei, et al., "Physical and Genetic Structure of the Maize Genome Reflects Its Complex Evolutionary History," PLoS Genet. 3:1254-1263 (Jul. 2007).
Wohlleben, et al., "Nucleotide Sequence of the Phosphinothricin N-Acetyltransferase Gene From Streptomyces Virido-Chromogenes TU494 and Its Expression in Nicotiana Tabacum," Gene 70(1):25-37 (Oct. 1988).
Woo, et al., "Genomics Analysis of Genes Expressed in Maize Endosperm Identifies Novel Seed Proteins and Clarifies Patterns of Zein Gene Expression," Plant Cell 13:2297-2317 (Oct. 2001).
Wright, et al., "High-Frequency Homologous Recombination in Plants Mediated by Zincfinger Nucleases," Plant J. 44:693-705 (Nov. 2005).

* cited by examiner

Figure 1: Depicts the relation of the ZFNs designed to bind the genomic locus of transgenic insert in Corn Event DAS-59132. Six ZFNs (E32 ZFN1-6) were identified from the yeast assay and four ZFNs were advanced for evaluation in plants.
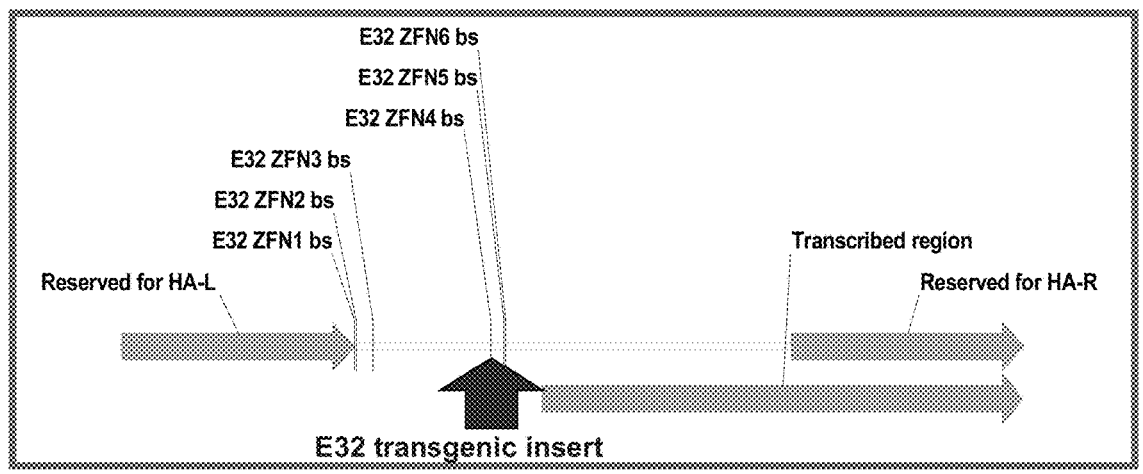
Figure 2: Plasmid map pDAB105906
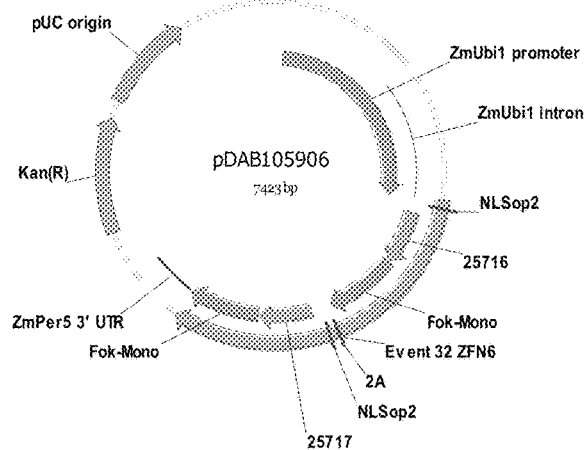

Figure 3: Plasmid map pDAB111809
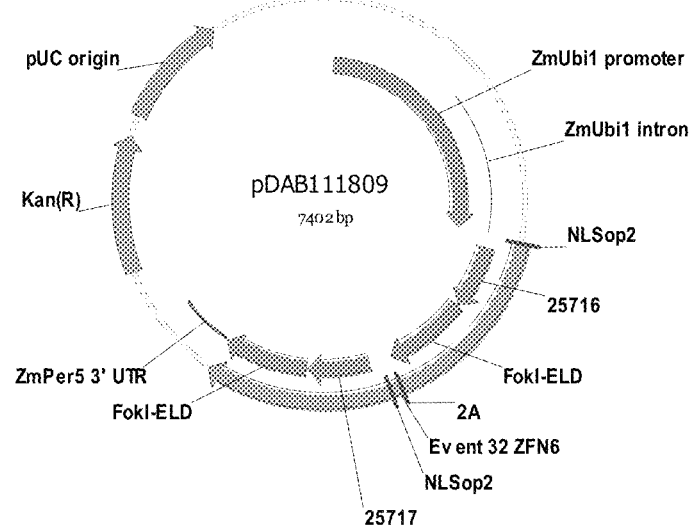
Figure 4: Plasmid map pDAB100655
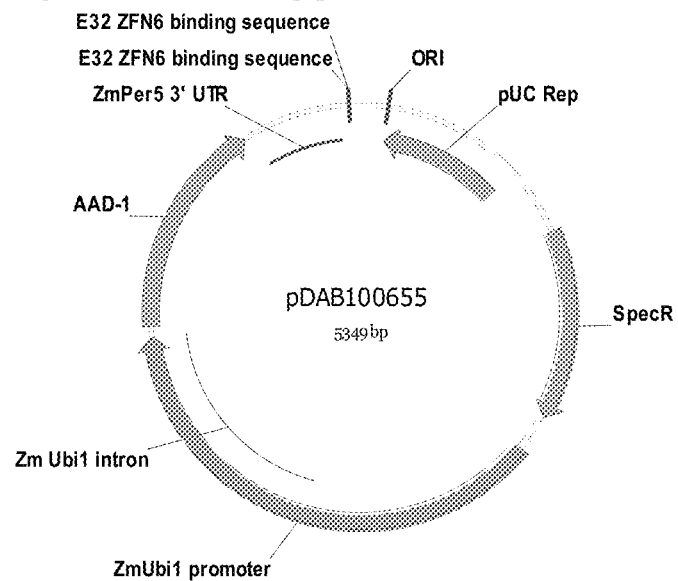

Figure 5: ZFN locus disruption of Corn Event DAS-59132 (the arrows indicate a disrupted genomic locus).
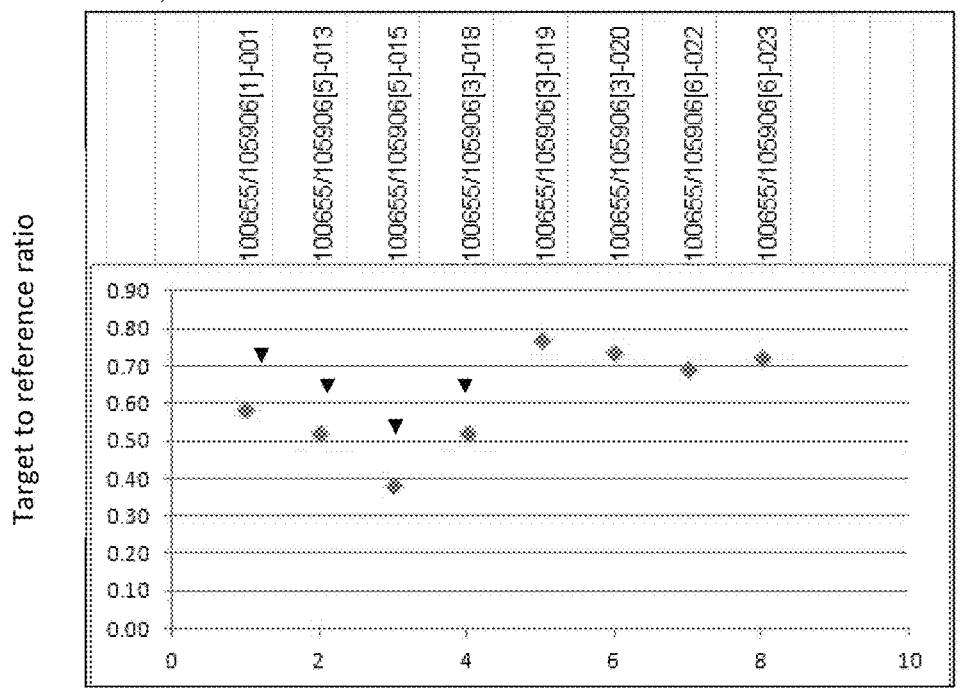
Figure 6: Plasmid map for pDAB108688 (control vector)
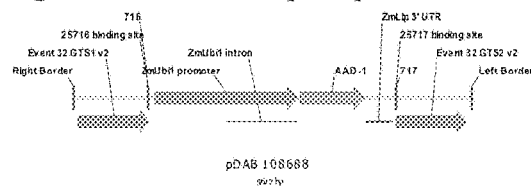

Figure 7: Plasmid map for pDAB108690 (targeting vector)
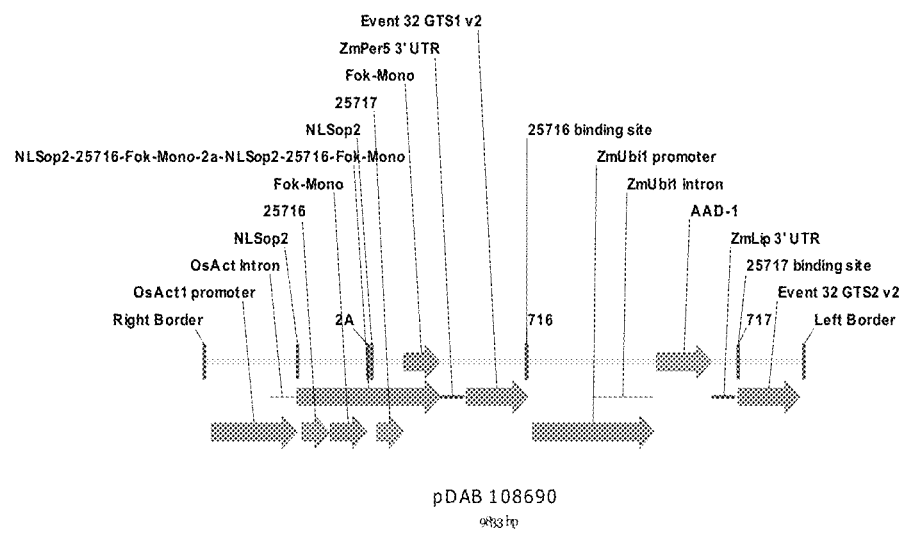
Figure 8: Primer and probe location for the ZFN disruption qPCR
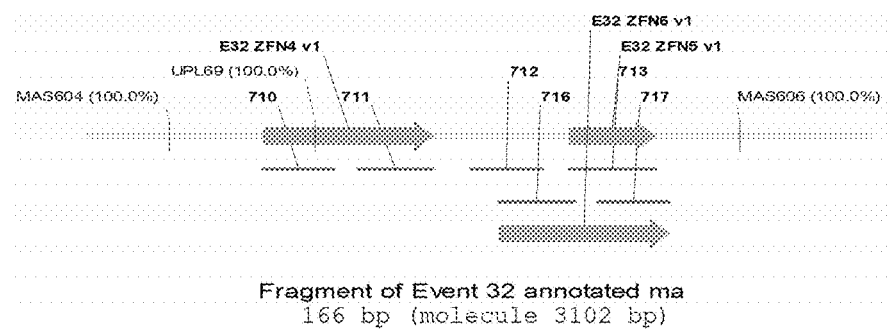

Figure 9: ZFN disruption assay (upper brackets indicate non-disrupted events and lower brackets show disrupted events).
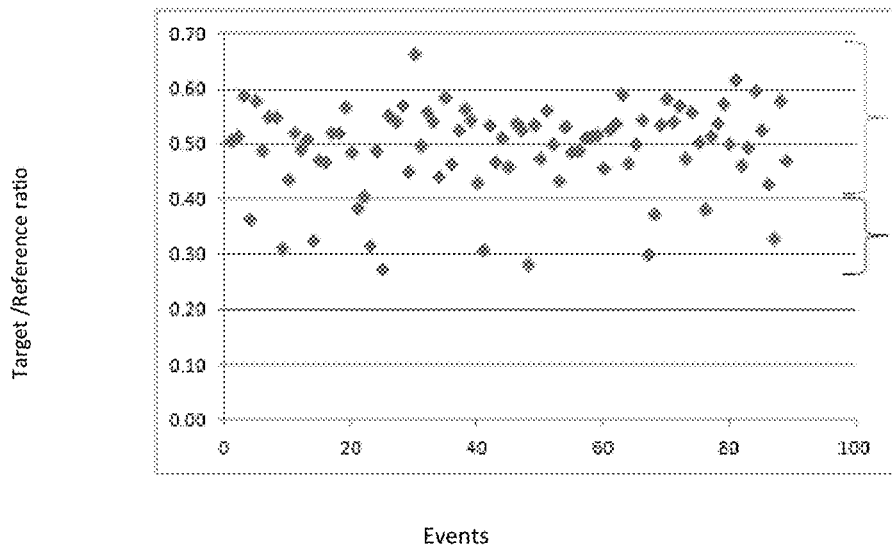
Events
Figure 10: Plasmid map of pDAB104179
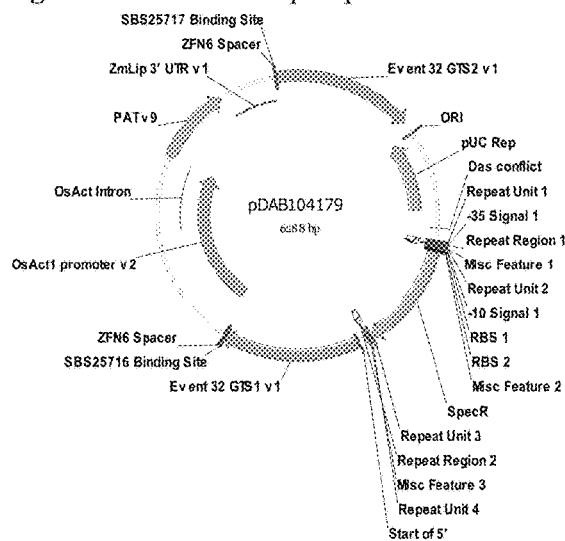

Figure 11: Primer and probe location for the ZFN disruption qPCR
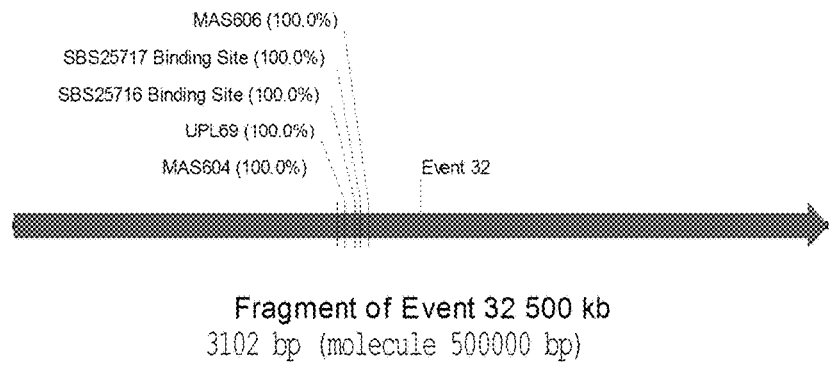
Figure 12: ZFN disruption assay (upper brackets indicate non-disrupted events negative and lower brackets show disrupted events)
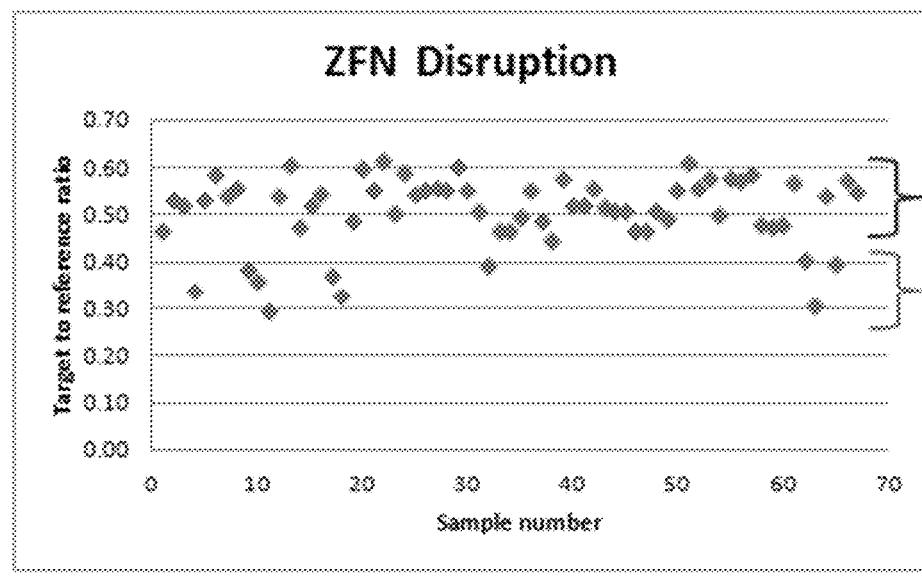

Figure 13: Primer location for in/out PCR
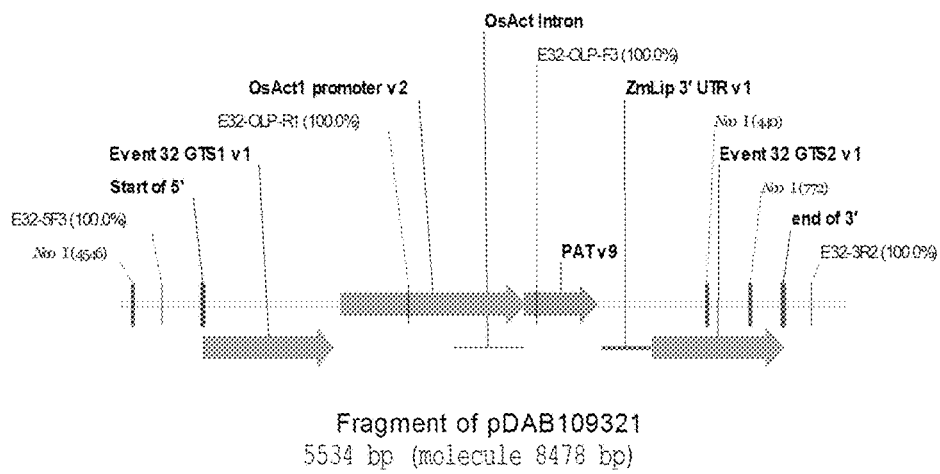
Figure 14: Southern Analysis strategy. Location of enzyme cut sites and primers for probe generation
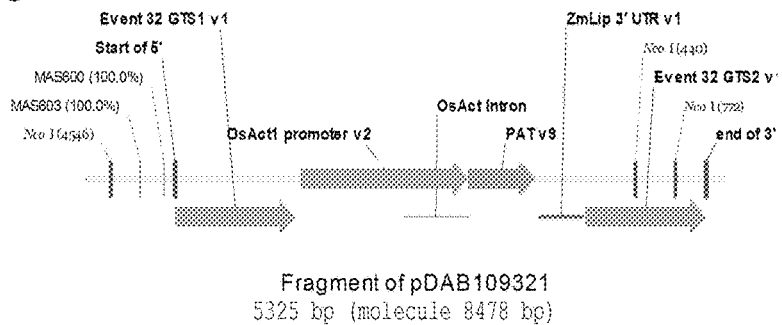

Figure 15: Plasmid map of pDAB107855
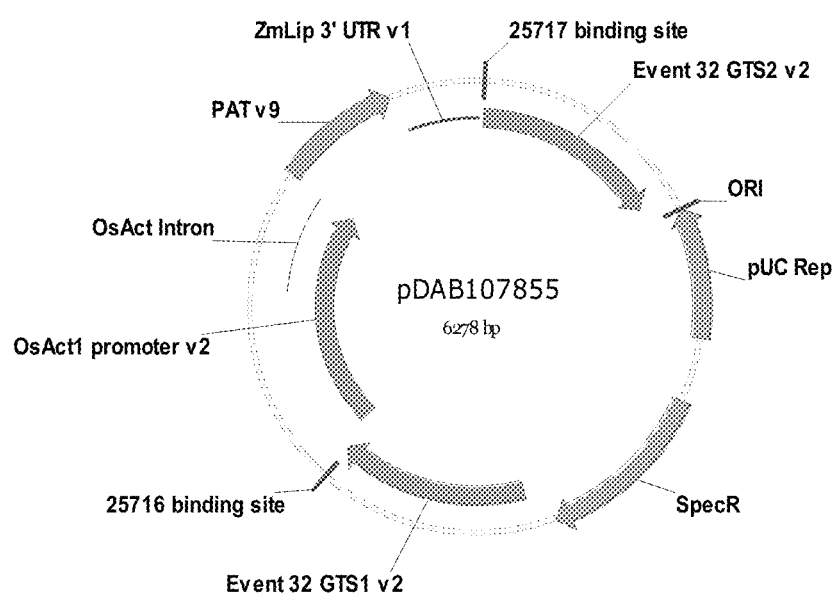

SEQUENCE LISTING

<160> NUMBER OF SEQ ID NOS: 73

<210> SEQ ID NO 1
<211> LENGTH: 3102
<212> TYPE: DNA
<213> ORGANISM: Artificial Sequence
<220> FEATURE:
<223> OTHER INFORMATION: Event 32 Locus

<400> SEQUENCE: 1

```
agttgggaag gcaaaacgaa tataagtgca ttcggattac tgtttagtcg agtcatattt      60
aaggaattca ttgtaaatgt tctaacctaa cctaagtatt aggcagctat ggctgatatg     120
gatctgattg gacttgattt atccatgata agtttaagag caactcaaag aggttaggta     180
tatatggttt tgtaaaggta aatttagtta atattagaaa aaaaaagtgt atccaatagg     240
ctctataaac aactcttcaa atttagtggc tttctatcca tccacctttg ctctctattt     300
ttggatagcc tgatttactc tctattcagt ccgtaggttt aatgagtctg ttggattagc     360
ctacactttt tctgtaaaat ctattttaga tagtagctaa atcagtaaat ttggctagta     420
tttttagcta ttctcttgga gtttgctata agaccagaac atgtaaattg gaagtttgtg     480
gacccggacg agaatgcatg acaaatccag agtattgatg atggaattca cctatttac      540 ccgactcttc cattgtgtcc atttctcatc atccccgggc gctttctgca tccggtacag     600
ctgacatgac acgttcacgc gttacatggc tgatggctca caagtcaccc ccacatgtct     660
agtgttcgcc caggcagatc gtcctcggcc tgcgctgccg tgctcttgcc gccgcttgct     720
tgggccctgc tggcgcccgc tgccgatcac acggcctacg cggtgcaggc agcgccaccg     780
aacccgcagt cttgttgtgc cgataggtgg cagtggcagt ggcactggca cggcacgcga     840
tcgatcgctc cgctcatctg ctgacagtgg atagagcagc gttggccgtt ggggccggat     900
ctccgtgaag cggtcgtccc tgctgtactg tgccgctatg gcgtgtcgct ttcgccatgt     960
tttcttttct tttttttttc ttttctttt tgctagggcg gtttctcgtt cgctggtaac    1020
agggaccact tcggttgatc cgttgaattt actgaaagag atgggaatgg tcgctgtgcc    1080
cgggacattg aatgagatgt tgtgtaagtg aatatggctt tagccttttg cgagtggggc    1140
ggcaatgcac ggcatgaact ataatttccg gtcaaacttt tgtgtggaaa tggatgctaa    1200
acgaacacaa accgggttta aaccagaggc cgacacggca cacacggcga cattcaccgc    1260
cggcttcctc cgtcgccact cggcacaagg ctcatcagtc gccgatgccc gatgcgatca    1320
acggaagcgg atgcccgct tctttagaat tggcacagga acactggcca ctgcccttga    1380
tgtgcaatta tgcctgcgaa agcctaggca acacacgcga ataaacgagc gaatgacacg    1440
gaaagctgat gtgtatgaa ttatacaaca ttatgggcca aaatattatt ctatccacca    1500
```

-continued

```
ttgtgtagcc acagcatcgg tatttgagtt gtgcgaggac aaatccctcg tgaggtcaaa    1560
aacagcaaat aataaaccca tctcctgaag acaccaaaaa aaaggagcag ctcctcgtgt    1620
caatgaacaa gcgtcacaag aaaagggagc acgtaaataa cctcttcaat tgcttcagca    1680
tgaaaagaac gggaagaaat gcaagtctac agaggaaagt gcagctgttt cggctgccat    1740
ggcaagttcc tacatgggcg aggaaaagct gaactggatt ccagtcttcg cgctgtcatg    1800
ctcagcttgc tttaggatgc ggcaatagtt cacctggatg aaaaagatac aagttagtct    1860
tgaagcagtc gagtggacat ccaaagtatc aaaatcgaaa gcttgtaaat ggggaaggaa    1920
atatacctct acccggaaaa gtttggtagg caaaataatc ccaacgccag cagagctccg    1980
gaacgtttgc cgaaattcag aagccgaaaa gttcttgtac tcaccctccg acagtttcgc    2040 aaggttttcca gcagtaagga atgcgtggcc atggattcca gcgtctctga atatcttgag    2100
gggcagatca aaagaaaggt cagcgaaggc agacacggcc agatcacctc ccaagtaatc    2160
ccttccaggg tcagccgagc cactctccga gttattaagg acatgcctcc gcgcctctgt    2220
tgggccaact ccccttaatc tgaaacccag cagagatgac ggtccgccca agctgcacac    2280
tggagaagaa ttacctccaa gataaaacct ctctggcact gatgaagtcg aattcatgaa    2340 tcccccctgca agcggtaaaa tgacaccgc tcctacacca acgttgagag cagcactata    2400
aaatcccaaa ggcacagcac cacgtacatc gaactcctga gagcaaaccc aacggcaata    2460
tttttgtaat agtgatggtc agaactgaga agatcagata aaattataca ctgatgcaat    2520
tatttcatag tttcgcccat gaactgtaag ggctagacaa agcaaaaagt aagacatgaa    2580
gggcaagaga ataacctgcc ggaaatatct caatcctttg ctattccata gaccaccaac    2640
ttgagaagtt gactgaaacg catatccttt cgttggccta agatgtgaat ccctcttatc    2700
aatcttgtat gtgtacttca atgcagaaag aaggttatgc cctaactgcc tccttatggc    2760
ctttgatgag acacgtgatg gatcagttaa ggtacgccac gcaaggttgt atgacaagtc    2820
atggttcctt gttgacagca aaccaaatga aaggccaagt aggcgctcct tgtatgatga    2880
aaacttcagc caatcttgtg atgacaaaga tgcccgagcc atcaatggtg ttggtattga    2940
tttaaacctc ggtaggcaga ctccaacacc aacctctgtt gtttggtccc aaccaaagga    3000
tcctgatgca tcccagatgt caccatagcc aaacaagttc ttcaacttaa gtgacccttc    3060
cagcgaccaa gatcttgcct acaagagtgg caagcacagt ca                      3102
```

```
<210> SEQ ID NO 2
<211> LENGTH: 28
<212> TYPE: DNA
<213> ORGANISM: Artificial Sequence
<220> FEATURE:
<223> OTHER INFORMATION: Zinc Finger Binding Sequence

<400> SEQUENCE: 2
cacaacaaga ctgcgggttc ggtggcgc                                        28

<210> SEQ ID NO 3
<211> LENGTH: 28
<212> TYPE: DNA
<213> ORGANISM: Artificial Sequence
<220> FEATURE:
<223> OTHER INFORMATION: Zinc Finger Binding Sequence

<400> SEQUENCE: 3
gataggtggc agtggcagtg gcactggc                                        28
```

```
<210> SEQ ID NO 4
<211> LENGTH: 28
<212> TYPE: DNA
<213> ORGANISM: Artificial Sequence
<220> FEATURE:
<223> OTHER INFORMATION: Zinc Finger Binding Sequence

<400> SEQUENCE: 4
tatcggcaca acaagactgc gggttcgg                                      28

<210> SEQ ID NO 5
<211> LENGTH: 28
<212> TYPE: DNA
<213> ORGANISM: Artificial Sequence
<220> FEATURE:
<223> OTHER INFORMATION: Zinc Finger Binding Sequence

<400> SEQUENCE: 5
tggcagtggc agtggcactg gcacggca                                      28

<210> SEQ ID NO 6
<211> LENGTH: 28
<212> TYPE: DNA
<213> ORGANISM: Artificial Sequence
<220> FEATURE:
<223> OTHER INFORMATION: Zinc Finger Binding Sequence

<400> SEQUENCE: 6
cagcagatga gcggagcgat cgatcgcg                                      28

<210> SEQ ID NO 7
<211> LENGTH: 28
<212> TYPE: DNA
<213> ORGANISM: Artificial Sequence
<220> FEATURE:
<223> OTHER INFORMATION: Zinc Finger Binding Sequence

<400> SEQUENCE: 7
cagtggatag agcagcgttg gccgttgg                                      28

<210> SEQ ID NO 8
<211> LENGTH: 28
<212> TYPE: DNA
<213> ORGANISM: Artificial Sequence
<220> FEATURE:
<223> OTHER INFORMATION: Zinc Finger Binding Sequence

<400> SEQUENCE: 8
aggaagccgg cggtgaatgt cgccgtgt                                      28

<210> SEQ ID NO 9
<211> LENGTH: 28
<212> TYPE: DNA
<213> ORGANISM: Artificial Sequence
<220> FEATURE:
<223> OTHER INFORMATION: Zinc Finger Binding Sequence

<400> SEQUENCE: 9
cgtcgccact cggcacaagg ctcatcag                                      28

<210> SEQ ID NO 10
<211> LENGTH: 28
<212> TYPE: DNA
<213> ORGANISM: Artificial Sequence
<220> FEATURE:
<223> OTHER INFORMATION: Zinc Finger Binding Sequence
```

```
<400> SEQUENCE: 10
atcgggcatc ggcgactgat gagccttg                                          28

<210> SEQ ID NO 11
<211> LENGTH: 28
<212> TYPE: DNA
<213> ORGANISM: Artificial Sequence
<220> FEATURE:
<223> OTHER INFORMATION: Zinc Finger Binding Sequence

<400> SEQUENCE: 11
gatcaacgga agcggatggc ccgcttct                                          28

<210> SEQ ID NO 12
<211> LENGTH: 28
<212> TYPE: DNA
<213> ORGANISM: Artificial Sequence
<220> FEATURE:
<223> OTHER INFORMATION: Zinc Finger Binding Sequence

<400> SEQUENCE: 12
tgatcgcatc gggcatcggc gactgatg                                          28

<210> SEQ ID NO 13
<211> LENGTH: 28
<212> TYPE: DNA
<213> ORGANISM: Artificial Sequence
<220> FEATURE:
<223> OTHER INFORMATION: Zinc Finger Binding Sequence

<400> SEQUENCE: 13
cggaagcgga tggcccgctt ctttagaa                                          28

<210> SEQ ID NO 14
<211> LENGTH: 18
<212> TYPE: DNA
<213> ORGANISM: Artificial Sequence
<220> FEATURE:
<223> OTHER INFORMATION: Primer Sequence

<400> SEQUENCE: 14
caggcagcgc caccgaac                                                     18

<210> SEQ ID NO 15
<211> LENGTH: 18
<212> TYPE: DNA
<213> ORGANISM: Artificial Sequence
<220> FEATURE:
<223> OTHER INFORMATION: Primer Sequence

<400> SEQUENCE: 15
cgatcgatcg cgtgccgt                                                     18

<210> SEQ ID NO 16
<211> LENGTH: 18
<212> TYPE: DNA
<213> ORGANISM: Artificial Sequence
<220> FEATURE:
<223> OTHER INFORMATION: Primer Sequence

<400> SEQUENCE: 16
ctggcacggc acgcgatc                                                     18

<210> SEQ ID NO 17
<211> LENGTH: 18
```

```
<212> TYPE: DNA
<213> ORGANISM: Artificial Sequence
<220> FEATURE:
<223> OTHER INFORMATION: Primer Sequence

<400> SEQUENCE: 17
cggagatccg gccccaac                                                  18

<210> SEQ ID NO 18
<211> LENGTH: 18
<212> TYPE: DNA
<213> ORGANISM: Artificial Sequence
<220> FEATURE:
<223> OTHER INFORMATION: Primer Sequence

<400> SEQUENCE: 18
gacacggcac acacggcg                                                  18

<210> SEQ ID NO 19
<211> LENGTH: 18
<212> TYPE: DNA
<213> ORGANISM: Artificial Sequence
<220> FEATURE:
<223> OTHER INFORMATION: Primer Sequence

<400> SEQUENCE: 19
tcgggcatcg gcgactga                                                  18

<210> SEQ ID NO 20
<211> LENGTH: 18
<212> TYPE: DNA
<213> ORGANISM: Artificial Sequence
<220> FEATURE:
<223> OTHER INFORMATION: Primer Sequence

<400> SEQUENCE: 20
actcggcaca aggctcat                                                  18

<210> SEQ ID NO 21
<211> LENGTH: 18
<212> TYPE: DNA
<213> ORGANISM: Artificial Sequence
<220> FEATURE:
<223> OTHER INFORMATION: Primer Sequence

<400> SEQUENCE: 21
cctgtgccaa ttctaaag                                                  18

<210> SEQ ID NO 22
<211> LENGTH: 18
<212> TYPE: DNA
<213> ORGANISM: Artificial Sequence
<220> FEATURE:
<223> OTHER INFORMATION: Primer Sequence

<400> SEQUENCE: 22
gcagtgcatg ttatgagc                                                  18

<210> SEQ ID NO 23
<211> LENGTH: 22
<212> TYPE: DNA
<213> ORGANISM: Artificial Sequence
<220> FEATURE:
<223> OTHER INFORMATION: Primer Sequence

<400> SEQUENCE: 23
```
caggacataa atgaactgaa tc                                          22

<210> SEQ ID NO 24
<211> LENGTH: 20
<212> TYPE: DNA
<213> ORGANISM: Artificial Sequence
<220> FEATURE:
<223> OTHER INFORMATION: Primer Sequence

<400> SEQUENCE: 24
tgttcggttc cctctaccaa                                             20

<210> SEQ ID NO 25
<211> LENGTH: 22
<212> TYPE: DNA
<213> ORGANISM: Artificial Sequence
<220> FEATURE:
<223> OTHER INFORMATION: Primer Sequence

<400> SEQUENCE: 25
caacatccat caccttgact ga                                          22

<210> SEQ ID NO 26
<211> LENGTH: 24
<212> TYPE: DNA
<213> ORGANISM: Artificial Sequence
<220> FEATURE:
<223> OTHER INFORMATION: Primer Sequence

<400> SEQUENCE: 26
cacagaaccg tcgcttcagc aaca                                        24

<210> SEQ ID NO 27
<211> LENGTH: 18
<212> TYPE: DNA
<213> ORGANISM: Artificial Sequence
<220> FEATURE:
<223> OTHER INFORMATION: Primer Sequence

<400> SEQUENCE: 27
tggcggacga cgacttgt                                               18

<210> SEQ ID NO 28
<211> LENGTH: 19
<212> TYPE: DNA
<213> ORGANISM: Artificial Sequence
<220> FEATURE:
<223> OTHER INFORMATION: Primer Sequence

<400> SEQUENCE: 28
aaagtttgga ggctgccgt                                              19

<210> SEQ ID NO 29
<211> LENGTH: 26
<212> TYPE: DNA
<213> ORGANISM: Artificial Sequence
<220> FEATURE:
<223> OTHER INFORMATION: Primer Sequence

<400> SEQUENCE: 29
cgagcagacc gccgtgtact tctacc                                      26

<210> SEQ ID NO 30
<211> LENGTH: 20
<212> TYPE: DNA
<213> ORGANISM: Artificial Sequence

```
<220> FEATURE:
<223> OTHER INFORMATION: Primer Sequence

<400> SEQUENCE: 30
gcccttacag ttcatgggcg                                              20

<210> SEQ ID NO 31
<211> LENGTH: 22
<212> TYPE: DNA
<213> ORGANISM: Artificial Sequence
<220> FEATURE:
<223> OTHER INFORMATION: Primer Sequence

<400> SEQUENCE: 31
gaccaagtcc ttgtctggga ca                                           22

<210> SEQ ID NO 32
<211> LENGTH: 21
<212> TYPE: DNA
<213> ORGANISM: Artificial Sequence
<220> FEATURE:
<223> OTHER INFORMATION: Primer Sequence

<400> SEQUENCE: 32
acaaacacgt cctccaaggc t                                            21

<210> SEQ ID NO 33
<211> LENGTH: 22
<212> TYPE: DNA
<213> ORGANISM: Artificial Sequence
<220> FEATURE:
<223> OTHER INFORMATION: Primer Sequence

<400> SEQUENCE: 33
gaccaagtcc ttgtctggga ca                                           22

<210> SEQ ID NO 34
<211> LENGTH: 226
<212> TYPE: DNA
<213> ORGANISM: Artificial Sequence
<220> FEATURE:
<223> OTHER INFORMATION: Probe Sequence

<400> SEQUENCE: 34
gtgcattcgg attactgttt agtcgagtca tatttaagga attcattgta aatgttctaa    60
cctaacctaa gtattaggca gctatggctg atatggatct gattggactt gatttatcca   120
tgataagttt aagagcaact caaagaggtt aggtatatat ggttttgtaa aggtaaattt   180
agttaatatt agaaaaaaaa agtgtatcca ataggctcta taaaca                 226

<210> SEQ ID NO 35
<211> LENGTH: 24
<212> TYPE: DNA
<213> ORGANISM: Artificial Sequence
<220> FEATURE:
<223> OTHER INFORMATION: Primer Sequence

<400> SEQUENCE: 35
acacggcaca cacggcgaca ttca                                         24

<210> SEQ ID NO 36
<211> LENGTH: 24
<212> TYPE: DNA
<213> ORGANISM: Artificial Sequence
<220> FEATURE:
```

<223> OTHER INFORMATION: Primer Sequence

<400> SEQUENCE: 36
agggcagtgg ccagtgttcc tgtg                                              24

<210> SEQ ID NO 37
<211> LENGTH: 18
<212> TYPE: DNA
<213> ORGANISM: Artificial Sequence
<220> FEATURE:
<223> OTHER INFORMATION: Primer Sequence

<400> SEQUENCE: 37
tggcggacga cgacttgt                                                     18

<210> SEQ ID NO 38
<211> LENGTH: 19
<212> TYPE: DNA
<213> ORGANISM: Artificial Sequence
<220> FEATURE:
<223> OTHER INFORMATION: Primer Sequence

<400> SEQUENCE: 38
aaagtttgga ggctgccgt                                                    19

<210> SEQ ID NO 39
<211> LENGTH: 26
<212> TYPE: DNA
<213> ORGANISM: Artificial Sequence
<220> FEATURE:
<223> OTHER INFORMATION: Primer Sequence

<400> SEQUENCE: 39
cgagcagacc gccgtgtact tctacc                                            26

<210> SEQ ID NO 40
<211> LENGTH: 29
<212> TYPE: DNA
<213> ORGANISM: Artificial Sequence
<220> FEATURE:
<223> OTHER INFORMATION: Primer Sequence

<400> SEQUENCE: 40
gaaggcaaaa cgaatataag tgcattcgg                                         29

<210> SEQ ID NO 41
<211> LENGTH: 21
<212> TYPE: DNA
<213> ORGANISM: Artificial Sequence
<220> FEATURE:
<223> OTHER INFORMATION: Primer Sequence

<400> SEQUENCE: 41
tcgtggatag cactttgggc t                                                 21

<210> SEQ ID NO 42
<211> LENGTH: 27
<212> TYPE: DNA
<213> ORGANISM: Artificial Sequence
<220> FEATURE:
<223> OTHER INFORMATION: Primer Sequence

<400> SEQUENCE: 42
tctacagtga actttaggac agagcca                                           27

-continued

<210> SEQ ID NO 43
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 43

Arg Ser Asp Asp Leu Ser Lys
1               5

<210> SEQ ID NO 44
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 44

Gln Ser Gly Ser Leu Thr Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 45

Arg Ser Asp Asn Leu Arg Glu
1               5

<210> SEQ ID NO 46
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 46

Gln Ser Gly Asp Leu Thr Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 47

Asp Thr Gly Ala Arg Leu Lys
1               5

<210> SEQ ID NO 48
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 48

Arg Ser Ala Asp Arg Lys Thr
1               5

<210> SEQ ID NO 49

```
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 49

Asp Arg Ser His Leu Ser Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 50

Thr Ser Gly Asn Leu Thr Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 51

Arg Ser Asp Asp Leu Ser Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 52

Gln Ser Ala Asn Arg Thr Lys
1               5

<210> SEQ ID NO 53
<211> LENGTH: 24
<212> TYPE: DNA
<213> ORGANISM: Artificial Sequence
<220> FEATURE:
<223> OTHER INFORMATION: Primer Sequence

<400> SEQUENCE: 53
acacggcaca cacggcgaca ttca                                          24

<210> SEQ ID NO 54
<211> LENGTH: 24
<212> TYPE: DNA
<213> ORGANISM: Artificial Sequence
<220> FEATURE:
<223> OTHER INFORMATION: Primer Sequence

<400> SEQUENCE: 54
agggcagtgg ccagtgttcc tgtg                                          24

<210> SEQ ID NO 55
<211> LENGTH: 18
<212> TYPE: DNA
<213> ORGANISM: Artificial Sequence
```

```
<220> FEATURE:
<223> OTHER INFORMATION: Primer Sequence

<400> SEQUENCE: 55
tggcggacga cgacttgt                                             18

<210> SEQ ID NO 56
<211> LENGTH: 19
<212> TYPE: DNA
<213> ORGANISM: Artificial Sequence
<220> FEATURE:
<223> OTHER INFORMATION: Primer Sequence

<400> SEQUENCE: 56
aaagtttgga ggctgccgt                                            19

<210> SEQ ID NO 57
<211> LENGTH: 26
<212> TYPE: DNA
<213> ORGANISM: Artificial Sequence
<220> FEATURE:
<223> OTHER INFORMATION: Primer Sequence

<400> SEQUENCE: 57
cgagcagacc gccgtgtact tctacc                                    26

<210> SEQ ID NO 58
<211> LENGTH: 20
<212> TYPE: DNA
<213> ORGANISM: Artificial Sequence
<220> FEATURE:
<223> OTHER INFORMATION: Primer Sequence

<400> SEQUENCE: 58
tgttcggttc cctctaccaa                                           20

<210> SEQ ID NO 59
<211> LENGTH: 22
<212> TYPE: DNA
<213> ORGANISM: Artificial Sequence
<220> FEATURE:
<223> OTHER INFORMATION: Primer Sequence

<400> SEQUENCE: 59
caacatccat caccttgact ga                                        22

<210> SEQ ID NO 60
<211> LENGTH: 24
<212> TYPE: DNA
<213> ORGANISM: Artificial Sequence
<220> FEATURE:
<223> OTHER INFORMATION: Primer Sequence

<400> SEQUENCE: 60
cacagaaccg tcgcttcagc aaca                                      24

<210> SEQ ID NO 61
<211> LENGTH: 4431
<212> TYPE: DNA
<213> ORGANISM: Artificial Sequence
<220> FEATURE:
<223> OTHER INFORMATION: pDAB104179 plasmid

<400> SEQUENCE: 61
tctctattca gtccgtaggt ttaatgagtc tgttggatta gcctacactt tttctgtaaa    60
```

```
atctatttta gatagtagct aaatcagtaa atttggctag tattttttagc tattctcttg    120 gagtttgcta taagaccaga acatgtaaat tggaagtttg tggacccgga cgagaatgca    180
tgacaaatcc agagtattga tgatggaatt cacctatttt acccgactct tccattgtgt    240
ccatttctca tcatccccgg gcgctttctg catccggtac agctgacatg acacgttcac    300
gcgttacatg gctgatggct cacaagtcac ccccacatgt ctagtgttcg cccaggcaga    360
tcgtcctcgg cctgcgctgc cgtgctcttg ccgccgcttg cttgggccct gctggcgccc    420
gctgccgatc acacggccta cgcggtgcag gcagcgccac cgaacccgca gtcttgttgt    480
gccgataggt ggcagtggca gtggcactgg cacggcacgc gatcgatcgc tccgctcatc    540
tgctgacagt ggatagagca gcgttggccg ttggggccgg atctccgtga agcggtcgtc    600
cctgctgtac tgtgccgcta tggcgtgtcg ctttcgccat gttttctttt cttttttttt    660 tcttttttctt tttgctaggg cggtttctcg ttcgctggta acagggacca cttcggttga    720
tccgttgaat ttactgaaag agatgggaat ggtcgctgtg cccgggacat gaatgagat    780 gttgtgtaag tgaatatggc tttagccttt tgcgagtggg gcggcaatgc acggcatgaa    840
ctataatttc cggtcaaact tttgtgtgga aatggatgct aaacgaacac aaaccgggtt    900
taaaccagag gccgacacgg cacacacggc gacattcacc gccggcttcc tccgtcgcca    960
ctcggcacaa ggctcatcag tcgccgatgc ccgatgcgat caacgtttat agcggccgca   1020
ttattatggc cggccattta aatatcgatt ctagtctcga ggtcattcat atgcttgaga   1080
agagagtcgg gatagtccaa aataaaacaa aggtaagatt acctggtcaa aagtgaaaac   1140
atcagttaaa aagtggtata aagtaaaata tcggtaataa aagtggccc aaagtgaaat    1200 ttactctttt ctactattat aaaaattgag gatgttttttg tcggtacttt gatacgtcat   1260
ttttgtatga attggttttt aagtttattc gcttttggaa atgcatatct gtatttgagt   1320
cgggttttaa gttcgtttgc ttttgtaaat acagagggat ttgtataaga aatatcttta   1380
aaaaaaccca tatgctaatt tgacataatt tttgagaaaa atatatattc aggcgaattc   1440
tcacaatgaa caataataag attaaaatag cttttcccccg ttgcagcgca tgggtatttt   1500
ttctagtaaa aataaaagat aaacttagac tcaaaacatt tacaaaaaca accccctaaag  1560 ttcctaaagc ccaaagtgct atccacgatc catagcaagc ccagcccaac ccaacccaac   1620
ccaacccacc ccagtccagc caactggaca atagtctcca cacccccccca ctatcaccgt   1680 gagttgtccg cacgcaccgc acgtctcgca gccaaaaaaa aaaaagaaa gaaaaaaaag    1740 aaaaagaaaa aacagcaggt gggtccgggt cgtgggggcc ggaaacgcga ggaggatcgc   1800
gagccagcga cgaggccggc cctccctccg cttccaaaga aacgcccccc atcgccacta   1860
tatacatacc ccccccctctc ctcccatccc ccaaccccta ccaccaccac caccaccacc   1920
tccacctcct ccccccctcgc tgccggacga cgcctccccc ctcccctcc gccgccgccg   1980 cgccggtaac caccccgccc ctctcctctt tctttctccg ttttttttttt ccgtctcggt   2040 ctcgatcttt ggccttggta gtttgggtgg gcgagaggcg gcttcgtgcg cgcccagatc   2100
ggtgcgcggg aggggcggga tctcgcggct ggggctctcg ccggcgtgga tccggcccgg   2160
atctcgcggg gaatgggct ctcggatgta gatctgcgat ccgccgttgt tggggagat    2220 gatgggggt ttaaaatttc cgccatgcta aacaagatca ggaagagggg aaaagggcac   2280
tatggtttat atttttatat atttctgctg cttcgtcagg cttagatgtg ctagatcttt   2340 cttttcttctt tttgtgggta gaatttgaat ccctcagcat tgttcatcgg tagtttttct   2400
tttcatgatt tgtgacaaat gcagcctcgt gcggagcttt tttgtaggta gaccatgtct   2460
```

-continued

```
ccggagagga gaccagttga gattaggcca gctacagcag ctgatatggc cgcggtttgt      2520
gatatcgtta accattacat tgagacgtct acagtgaact ttaggacaga gccacaaaca      2580
ccacaagagt ggattgatga tctagagagg ttgcaagata gatacccttg gttggttgct      2640
gaggttgagg gtgttgtggc tggtattgct tacgctgggc cctggaaggc taggaacgct      2700
tacgattgga cagttgagag tactgtttac gtgtcacata ggcatcaaag gttgggccta      2760
ggatccacat tgtacacaca tttgcttaag tctatggagg cgcaaggttt taagtctgtg      2820
gttgctgtta taggccttcc aaacgatcca tctgttaggt tgcatgaggc tttgggatac      2880
acagcccgtg gtacattgcg cgcagctgga tacaagcatg gtggatggca tgatgttggt      2940
ttttggcaaa gggattttga gttgccagct cctccaaggc cagttaggcc agttacccag      3000
atctgactga gcttgagctt atgagcttat gagcttagag ctcggtcgca gcgtgtgcgt      3060
gtccgtcgta cgttctggcc ggccgggcct tgggcgcgcg atcagaagcg ttgcgttggc      3120
gtgtgtgtgc ttctggtttg ctttaatttt accaagtttg tttcaaggtg gatcgcgtgg      3180
tcaaggcccg tgtgctttaa agacccaccg gcactggcag tgagtgttgc tgcttgtgta      3240
ggctttggta cgtatgggct ttatttgctt ctggatgttg tgtactactt gggtttgttg      3300
aattattatg agcagttgcg tattgtaatt cagctgggct acctggacat tgttatgtat      3360
taataaatgc tttgctttct tctaaagatc tttaagtgct actagattaa ttaactcgag      3420
gtcgaccaac ggaagcggat ggcccgcttc tttagaattg gcacaggaac actggccact      3480
gcccttgatg tgcaattatg cctgcgaaag cctaggcaac acgcgaatag aaacgagcga      3540
atgacacgga aagctgatgt ggtatgaatt atacaacatt atgggccaaa atattattct      3600
atccaccatt gtgtagccac agcatcggta tttgagttgt gcgaggacaa atccctcgtg      3660
aggtcaaaaa cagcaaataa taaacccatc tcctgaagac accaaaaaaa aggagcagct      3720
cctcgtgtca atgaacaagc gtcacaagaa aagggagcac gtaaataacc tcttcaattg      3780
cttcagcatg aaaagaacgg gaagaaatgc aagtctacag aggaaagtgc agctgtttcg      3840
gctgccatgg caagttccta catgggcgag gaaaagctga actggattcc agtcttcgcg      3900
ctgtcatgct cagcttgctt taggatgcgg caatagttcc cctggatgaa aaagatacaa      3960
gttagtcttg aagcagtcga gtggacatcc aaagtatcaa aatcgaaagc ttgtaaatgg      4020
ggaaggaaat atacctctac ccggaaaagt ttggtaggca aaataatccc aacgccagca      4080
gagctccgga acgtttgccg aaattcagaa gccgaaaagt tcttgtactc accctccgac      4140
agtttcgcaa ggtttccagc agtaaggaat gcgtggccat ggattccagc gtctctgaat      4200
atcttgaggg gcagatcaaa agaaaggtca gcgaaggcag acacggccag atcacctccc      4260
aagtaatccc ttccagggtc agccgagcca ctctccgagt tattaaggac atgcctccgc      4320
gcctctgttg ggccaactcc ccttaatctg aaacccagca gagatgacgg tccgcccaag      4380
ctgcacactg gagaagaatt acctccaaga taaaacctct ctggcactga t                4431
```

<210> SEQ ID NO 62
<211> LENGTH: 29
<212> TYPE: DNA
<213> ORGANISM: Artificial Sequence
<220> FEATURE:
<223> OTHER INFORMATION: Primer Sequence

<400> SEQUENCE: 62
acaagagtgg attgatgatc tagagaggt                                         29

<210> SEQ ID NO 63
<211> LENGTH: 29
<212> TYPE: DNA
<213> ORGANISM: Artificial Sequence
<220> FEATURE:
<223> OTHER INFORMATION: Primer Sequence

<400> SEQUENCE: 63
ctttgatgcc tatgtgacac gtaaacagt                              29

<210> SEQ ID NO 64
<211> LENGTH: 29
<212> TYPE: DNA
<213> ORGANISM: Artificial Sequence
<220> FEATURE:
<223> OTHER INFORMATION: Primer Sequence

<400> SEQUENCE: 64
ggtgttgtgg ctggtattgc ttacgctgg                              29

<210> SEQ ID NO 65
<211> LENGTH: 21
<212> TYPE: DNA
<213> ORGANISM: Artificial Sequence
<220> FEATURE:
<223> OTHER INFORMATION: Primer Sequence

<400> SEQUENCE: 65
cctgctccac taccagtaca a                                      21

<210> SEQ ID NO 66
<211> LENGTH: 21
<212> TYPE: DNA
<213> ORGANISM: Artificial Sequence
<220> FEATURE:
<223> OTHER INFORMATION: Primer Sequence

<400> SEQUENCE: 66
gtccaagaag gtgaccttct c                                      21

<210> SEQ ID NO 67
<211> LENGTH: 23
<212> TYPE: DNA
<213> ORGANISM: Artificial Sequence
<220> FEATURE:
<223> OTHER INFORMATION: Primer Sequence

<400> SEQUENCE: 67
agatcaccga ctttgcgctc ttt                                    23

<210> SEQ ID NO 68
<211> LENGTH: 29
<212> TYPE: DNA
<213> ORGANISM: Artificial Sequence
<220> FEATURE:
<223> OTHER INFORMATION: Primer Sequence

<400> SEQUENCE: 68
gaaggcaaaa cgaatataag tgcattcgg                              29

<210> SEQ ID NO 69
<211> LENGTH: 27
<212> TYPE: DNA
<213> ORGANISM: Artificial Sequence
<220> FEATURE:
<223> OTHER INFORMATION: Primer Sequence

```
<400> SEQUENCE: 69
tctacagtga actttaggac agagcca                                          27

<210> SEQ ID NO 70
<211> LENGTH: 21
<212> TYPE: DNA
<213> ORGANISM: Artificial Sequence
<220> FEATURE:
<223> OTHER INFORMATION: Primer Sequence

<400> SEQUENCE: 70
tcgtggatag cactttgggc t                                                21

<210> SEQ ID NO 71
<211> LENGTH: 20
<212> TYPE: DNA
<213> ORGANISM: Artificial Sequence
<220> FEATURE:
<223> OTHER INFORMATION: Primer Sequence

<400> SEQUENCE: 71
gcccttacag ttcatgggcg                                                  20

<210> SEQ ID NO 72
<211> LENGTH: 24
<212> TYPE: DNA
<213> ORGANISM: Artificial Sequence
<220> FEATURE:
<223> OTHER INFORMATION: Primer Sequence

<400> SEQUENCE: 72
tgtttataga gcctattgga taca                                             24

<210> SEQ ID NO 73
<211> LENGTH: 25
<212> TYPE: DNA
<213> ORGANISM: Artificial Sequence
<220> FEATURE:
<223> OTHER INFORMATION: Primer Sequence

<400> SEQUENCE: 73
agtgcattcg gattactgtt tagtc                                            25
```

PRECISION GENE TARGETING TO A PARTICULAR LOCUS IN MAIZE

CROSS-REFERENCE TO RELATED APPLICATIONS

This application is a continuation application of U.S. application Ser. No. 14/105,563, filed on Dec. 13, 2013, which claims the benefit of the filing date of U.S. Provisional Patent Application Ser. Nos. 61/820,231, filed May 7, 2013, and 61/736,856, filed Dec. 13, 2012, the entire disclosures of all of which are incorporated herein by reference.

TECHNICAL FIELD

This disclosure relates to the targeted stable integration of foreign polynucleotides into one particular locus of the maize genome through the use of zinc finger nucleases.

REFERENCE TO SEQUENCE LISTING SUBMITTED ELECTRONICALLY

The official copy of the sequence listing is submitted electronically via EFS-Web as an ASCII formatted sequence listing with a file named "74381_ST25.txt", created on Nov. 26, 2013, and having a size of 23.7 kilobytes and is filed concurrently with the specification. The sequence listing contained in this ASCII formatted document is part of the specification and is herein incorporated by reference in its entirety.

BACKGROUND

The genomic locus of Corn Event DAS-59132 is described in U.S. Pat. No. 8,273,535, METHODS FOR DETECTION OF CORN EVENT DAS-59132. The transgene expression cassette integrated into chromosome 8 of the B73 maize genome derived region of Hi-II maize germplasm (D. D. Songstad, W. L. Petersen, C. L. Armstrong, *American Journal of Botany*, Vol. 79, pp. 761-764, 1992) as a full length T-strand insert. In addition, the genomic DNA surrounding the transgenic locus lacked any large deletions relative to the native B73 sequence, and was generally devoid of repetitive elements except for a single, small repetitive element. Extensive field studies revealed that the presence of the event did not adversely affect normal growth and development of plants that carried the event. Moreover, corn lines bearing the event retained the agronomic and breeding characteristics comparable in agronomic performance to non-transformed isolines. Hence the genomic locus in which Corn Event DAS-59132 integrated represents an excellent endogenous genomic locus in maize for the targeted integration of other transgenic constructs and hereinafter is referred to as the E32 or Event32 locus.

Targeted genome modification of plants has been a longstanding and elusive goal of both applied and basic research. Methods and compositions to target and cleave genomic DNA by site specific nucleases are being developed to reach this goal. Site specific nucleases include but are not limited to (Zinc Finger Nucleases (ZFNs), Meganucleases, TALENS and CRISPR/Cas with an engineered crRNA/tracr RNA, see Burgess; et al; *Nature Reviews Genetics* 14, 80-81 (February 2013)). The site specific cleavage of genomic loci by ZFNs can be used, for example, to induce targeted mutagenesis, induce targeted deletions of cellular DNA sequences, and facilitate targeted recombination of an exogenous donor DNA polynucleotide within a predetermined genomic locus. See, for example, U.S. Patent Publication No. 20030232410; 20050208489; 20050026157; 20050064474; and 20060188987, and International Patent Publication No. WO 2007/014275, the disclosures of which are incorporated by reference in their entireties for all purposes. U.S. Patent Publication No. 20080182332 describes use of non-canonical zinc finger nucleases (ZFNs) for targeted modification of plant genomes and U.S. Patent Publication No. 20090205083 describes ZFN-mediated targeted modification of a plant EPSPs genomic locus. In addition, Moehle et al. (2007) Proc. Natl. Acad. Sci. USA 104(9): 3055-3060 describe using designed ZFNs for targeted gene addition at a specified genomic locus. Current methods of targeting typically involve co-transformation of plant tissue with a donor DNA polynucleotide containing at least one transgene and a site specific nuclease which is designed to bind and cleave a specific genomic locus. This causes the donor DNA polynucleotide to stably insert within the cleaved genomic locus resulting in targeted gene addition at a specified genomic locus.

BRIEF SUMMARY OF THE INVENTION

The presently claimed invention is a method for integrating one or more functional exogenous nucleic acid sequences into the genome of a maize cell having an E32 locus. The method comprises making a double-stranded cleavage in the E32 locus using one or more zinc finger nucleases comprising a zinc finger binding domain that binds to a target site selected from the group shown in Table 1B. This results in the integration of a functional polynucleotide comprising the one or more exogenous sequences into the genome of the maize cell within the E32 locus. The method optionally includes expressing a gene product encoded and controlled by the one or more exogenous sequences.

BRIEF DESCRIPTION OF THE DRAWINGS

FIG. 1 depicts the relation of the ZFNs designed to bind the E32 locus of. Six ZFNs (E32 ZFN1-6) were indentified from the yeast assay and four ZFNs were advanced for evaluation in plants.

FIG. 2 is a plasmid map of pDAB105906.

FIG. 3 is a plasmid map of pDAB111809.

FIG. 4 is a plasmid map of pDAB100655 and represents a typical donor construct in which other desirable coding sequences, including but not limited to PAT can be substituted for the AAD-1 region.

FIG. 5 is a ZFN locus disruption graph of the E32 locus with arrows indicating a disrupted genomic locus.

FIG. 6 is a plasmid map for pDAB108688 (control vector).

FIG. 7 is a plasmid map for pDAB108690 (targeting vector).

FIG. 8 shows the primer and probe location for the ZFN disruption qPCR.

FIG. 9 is a ZFN disruption assay graph (upper brackets indicate non-disrupted events and lower brackets show disrupted events).

FIG. 10 is a plasmid map of pDAB104179.

FIG. 11 shows the primer and probe location for the ZFN disruption qPCR.

FIG. 12 is a ZFN disruption assay graph (upper brackets indicate non-disrupted events negative and lower brackets show disrupted events).

FIG. 13 shows the primer location for in/out PCR.

FIG. 14 is a Southern analysis strategy showing the location of enzyme cut sites and primers for probe generation.

FIG. 15 is a plasmid map of pDAB107855.

DETAILED DESCRIPTION OF THE INVENTION

The full length DNA molecule (PHI17662A) used to transform Corn Event DAS-59132, the 3' end of the genomic flanking sequence, and the PHI17662A/3' maize genome junction are described in the disclosure of U.S. Pat. No. 8,273,535. The E32 locus is described by SEQ ID NO:1 and relates to the genomic flanking regions of Corn Event DAS-59132 that were used to identify genomic target sequences for designing zinc finger protein binding domains for exogenous gene insertion. These target sites include but are not limited to those described in Table 1B. After having identified the E32 locus as a highly desirable location for inserting exogenous genes which is one embodiment of this invention, it is well within the skilled artisans purview to identify and use other target sites within the E32 locus.

SEQ ID NO:1 is provided as the following sequence;

agttgggaaggcaaaacgaatataagtgcattcggattactgtttagtcg agtcatatttaaggaattcattgtaaatgttctaacctaacctaagtatt aggcagctatggctgatatggatctgattggacttgatttatccatgata agtttaagagcaactcaaagaggttaggtatatatggttttgtaaaggta aatttagttaatattagaaaaaaaaagtgtatccaataggctctataaac aactcttcaaatttagtggctttctatccatccacctttgctctctattt ttggatagcctgatttactctctattcagtccgtaggtttaatgagtctg ttggattagcctacacttttctgtaaaatctattttagatagtagctaa atcagtaaatttggctagtatttttagctattctcttggagtttgctata agaccagaacatgtaaattggaagtttgtggaccccggacgagaatgcatg acaaatccagagtattgatgatggaattcacctattttacccgactcttc cattgtgtccatttctcatcatccccgggcgctttctgcatccggtacag ctgacatgacacgttcacgcgttacatggctgatggctcacaagtcaccc ccacatgtctagtgttcgcccaggcagatcgtcctcggcctgcgctgccg tgctcttgccgccgcttgcttgggccctgctggcgcccgctgccgatcac acggcctacgcggtgcaggcagcgccaccgaacccgcagtcttgttgtgc cgataggtggcagtggcagtggcactggcacggcacgcgatcgatcgctc cgctcatctgctgacagtggatagagcagcgttggccgttggggccggat ctccgtgaagcggtcgtccctgctgtactgtgccgctatggcgtgtcgct ttcgccatgttttctttttctttttttttctttttctttttgctagggcg gtttctcgttcgctggtaacagggaccacttcggttgatccgttgaattt actgaaagagatgggaatggtcgctgtgcccgggacattgaatgagatgt tgtgtaagtgaatatggctttagccttttgcgagtggggcggcaatgcac ggcatgaactataatttccggtcaaacttttgtgtggaaatggatgctaa acgaacacaaacccgggtttaaaccagaggccgacacggcacacacggcga cattcaccgccggcttcctccgtcgccactcggcacaaggctcatcagtc gccgatgcccgatgcgatcaacggaagcggatggcccgcttctttagaat tggcacaggaacactggccactgcccttgatgtgcaattatgcctgcgaa agcctaggcaacacacgcgaataaacgagcgaatgacacggaaagctgat gtggtatgaattatacaacattatgggccaaaatattattctatccacca ttgtgtagccacagcatcggtatttgagttgtgcgaggacaaatccctcg tgaggtcaaaaacagcaaataataaacccatctcctgaagcacccaaaaa aaaggagcagctcctcgtgtcaatgaacaagcgtcacaagaaaagggagc acgtaaataacctcttcaattgcttcagcatgaaaagaacgggaagaaat gcaagtctacagaggaaagtgcagctgtttcggctgccatggcaagttcc tacatgggcgaggaaaagctgaactggattccagtcttcgcgctgtcatg ctcagcttgctttaggatgcggcaatagttcacctggatgaaaaagatac aagttagtcttgaagcagtcgagtggacatccaaagtatcaaatcgaaa gcttgtaaatggggaaggaaatatacctctacccggaaaagtttggtagg caaaataatcccaacgccagcagagctccggaacgtttgccgaaattcag aagccgaaaagttcttgtactcaccctccgacagtttcgcaaggtttcca gcagtaaggaatgcgtggccatggattccagcgtctctgaatatcttgag gggcagatcaaaagaaaggtcagcgaaggcagacacggccagatcacctc ccaagtaatcccttccagggtcagccgagccactctccgagttattaagg acatgcctccgcgcctctgtttgggccaactcccctttaatctgaaacccag cagagatgacggtccgcccaagctgcacactggagaagaattacctccaa gataaaacctctctggcactgatgaagtcgaattcatgaatcccctgca agcggtaaaatgacacccgctcctacaccaacgttgagagcagcactata aaatcccaaaggcacagcaccacgtacatcgaactcctgagagcaaaccc aacggcaatatttttgtaatagtgatggtcagaactgagaagatcagata aaattatacactgatgcaatttatttcatagtttcgcccatgaactgtaag ggctagacaaagcaaaaagtaagacatgaagggcaagagaataaccctgcc ggaaatatctcaatcctttgctattccatagaccaccaacttgagaagtt gactgaaacgcatatcctttcgttggcctaagatgtgaatccctcttatc aatcttgtatgtgtacttcaatgcagaaagaaggttatgccctaactgcc tccttatggcctttgatgagacacgtgatggatcagttaaggtacgccac gcaaggttgtatgacaagtcatggttccttgttgacagcaaaccaaatga aaggccaagtaggcgctccttgtatgatgaaaacttcagccaatcttgtg atgacaaagatgcccgagccatcaatggtgttggtattgatttaaacctc ggtaggcagactccaacaccaacctctgttgtttggtcccaaccaaagga tcctgatgcatcccagatgtcaccatagccaaacaagttcttcaacttaa gtgacccttccagcgaccaagatcttgcctacaagagtggcaagcacagt ca The present disclosure further relates to methods and compositions for targeted integration into the maize E32 locus using ZFNs and a gene donor construct. Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolfe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant (Kd) of $10^{-6}$ M or lower. "Affinity" refers to the strength of binding: increased binding affinity being correlated with a lower binding constant (Kd).

A "binding protein" is a protein that is able to bind non-covalently to another molecule. A binding protein can bind to, for example, a DNA molecule (a DNA-binding protein), a RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261 and 6,794,136; see also WO 98/53058; WO 98/53059; WO 98/53060; WO 02/016536 and WO 03/016496.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage. A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule induced by heat shock is an exogenous molecule with respect to a non heat-shocked cell. An exogenous molecule can comprise, for example, a coding sequence for any polypeptide or fragment thereof, a functioning version of a malfunctioning endogenous molecule or a malfunctioning version of a normally-functioning endogenous molecule. Additionally, an exogenous molecule can comprise a coding sequence from another species.

Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

A "product of an exogenous nucleic acid" includes both polynucleotide and polypeptide products, for example, transcription products (polynucleotides such as RNA) and translation products (polypeptides) and the products of gene expression and gene products.

A "fusion" molecule is a molecule in which two or more subunit molecules are linked, for example, covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

For the purposes of the present disclosure, a "gene," includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

The disclosed methods and compositions include fusion proteins comprising a cleavage domain and a DNA-binding domain (ZFP) in which the DNA-binding domain by binding to a sequence in the E32 locus directs the activity of the cleavage domain to the vicinity of the sequence and, hence, induces a double stranded break) in the E32 locus. As set forth elsewhere in this disclosure, a zinc finger domain can be engineered to bind to virtually any desired sequence. Accordingly, one or more DNA-binding domains can be engineered to bind to one or more sequences in the E32 locus. Expression of a fusion protein comprising a DNA-binding domain and a cleavage domain in a cell, effects cleavage at or near the target site.

Selection of a target site in the E32 locus for binding by a zinc finger domain can be accomplished, for example, according to the methods disclosed in U.S. Pat. No. 6,453,242 that also discloses methods for designing ZFPs to bind to a selected sequence. It will be clear to those skilled in the art that simple visual inspection of a nucleotide sequence can also be used for selection of a target site. Accordingly, any means for target site selection can be used in the methods described herein.

For ZFP DNA-binding domains, target sites are generally composed of a plurality of adjacent target subsites. A target subsite refers to the sequence, usually either a nucleotide triplet or a nucleotide quadruplet which may overlap by one nucleotide with an adjacent quadruplet, that is bound by an individual zinc finger. See, for example, WO 02/077227. The strand with which a zinc finger protein makes most contacts is designated the target strand "primary recognition strand," or "primary contact strand," some zinc finger proteins bind to a three base triplet in the target strand and a fourth base on the non-target strand. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also consistent with the invention.

It is not necessary for a target site to be a multiple of three nucleotides. In cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites.

Distance between target sites refers to the number of nucleotides or nucleotide pairs intervening between two target sites as measured from the edges of the sequences nearest each other. In certain embodiments in which cleavage depends on the binding of two zinc finger domain/cleavage half-domain fusion molecules to separate target sites, the two target sites can be on opposite DNA strands. In other embodiments, both target sites are on the same DNA strand.

For targeted integration into the E32 locus, one or more ZFPs are engineered to bind a target site at or near the predetermined cleavage site, and a fusion protein comprising the engineered DNA-binding domain and a cleavage domain is expressed in the cell. Upon binding of the zinc finger portion of the fusion protein to the target site, the DNA is cleaved, preferably via a double-stranded break, near the target site by the cleavage domain.

The presence of a double-stranded break in the Event32 locus facilitates integration of exogenous sequences via homologous recombination or via non-homology directed repair mechanisms. Thus, the polynucleotide comprising the exogenous sequence to be inserted into the Event32 locus will include one or more regions of homology with E32 to facilitate homologous recombination.

In addition to the fusion molecules described herein, targeted replacement of a selected genomic sequence also involves the introduction of a donor sequence. The donor sequence can be introduced into the cell prior to, concurrently with, or subsequent to, expression of the fusion protein(s). The donor polynucleotide contains sufficient homology to E32 to support homologous recombination between it and the E32 genomic sequence to which it bears homology. Approximately 25, 50, 100, 200, 500, 750, 1,000, 1,500, 2,000 nucleotides or more of sequence homology between a donor and a genomic sequence, or any integral value between 10 and 2,000 nucleotides or more, will support homologous recombination. In certain embodiments, the homology arms are less than 1,000 base pairs in length. In other embodiments, the homology arms are less than 750 base pairs in length.

Donor sequences can range in length from 10 to 50,000 base pairs or any integral value of nucleotides between or longer. It will be readily apparent that the donor sequence is typically not identical to the genomic sequence that it replaces. Additionally, donor sequences can comprise a vector molecule containing sequences that are not homologous to the replaced region. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

A donor molecule can contain several, discontinuous regions of homology to cellular chromatin. For example, for targeted insertion of sequences not normally present in a region of interest, said sequences can be present in a donor nucleic acid molecule and flanked by regions of homology to a gene sequence in the region of interest.

Donor molecules can also be inserted into the E32 locus to serve as a reservoir for later use. For example, a donor molecule containing a mutation of interest may be inserted in the E32 locus. Next, ZFNs specific to the gene of interest can be introduced which will cleave both the endogenous locus and the donor molecule in the E32 locus which contains the mutation of interest. The resulting double stranded break in the genome can then become the integration site for the donor molecule released from the E32 locus. In this way, the efficiency of targeted integration of a donor sequence at any region of interest can be greatly increased since the method does not rely on simultaneous uptake of both the nucleic acids encoding the ZFNs and those donor sequences.

Donor molecules can also be inserted into the E32 locus to serve as a target site for subsequent insertions. For example, a donor molecule comprised of DNA sequences that contain recognition sites for additional ZFN designs may be inserted into the locus. Subsequently, additional ZFN designs may be generated and expressed in cells such that the original donor molecule is cleaved and modified by repair or homologous recombination. In this way, reiterative integrations of donor molecules may occur at the E32 locus.

Any exogenous sequence can be introduced into the E32 locus as described herein. Exemplary exogenous sequences include, but are not limited to any polypeptide coding sequence (e.g., cDNAs), promoter, enhancer and other regulatory sequences (e.g., interfering RNA sequences, shRNA expression cassettes, epitope tags, marker genes, cleavage enzyme recognition sites and various types of expression constructs. Such sequences can be readily obtained using standard molecular biological techniques (cloning, synthesis, etc.) and/or are commercially available.

To express ZFNs, sequences encoding the fusion proteins are typically subcloned into an expression vector that contains a promoter to direct transcription. Suitable bacterial and eukaryotic promoters are well known in the art and described, e.g., in Sambrook et al., Molecular Cloning, A Laboratory Manual (2nd ed. 1989; 3.sup rd ed., 2001); Kriegler, Gene Transfer and Expression: A Laboratory Manual (1990); and Current Protocols in Molecular Biology (Ausubel et al., supra. Bacterial expression systems for expressing the ZFNs are available in, e.g., *E. coli, Bacillus* sp., and *Salmonella* (Palva et al., Gene 22:229-235 (1983)). Kits for such expression systems are commercially available. Eukaryotic expression systems for mammalian cells, yeast, and insect cells are well known by those of skill in the art and are also commercially available.

The particular expression vector used to transport the genetic material into the cell is selected with regard to the intended use of the fusion proteins, e.g., expression in plants, animals, bacteria, fungus, protozoa, etc. (see expression vectors described below). Standard bacterial and animal expression vectors are known in the art and are described in detail, for example, U.S. Patent Publication 20050064474A1 and International Patent Publications WO05/084190, WO05/014791 and WO03/080809.

Standard transfection methods can be used to produce bacterial, mammalian, yeast or insect cell lines that express large quantities of protein, which can then be purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds., 1983).

Any of the well known procedures for introducing foreign nucleotide sequences into such host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

As noted above, DNA constructs may be introduced into the genome of a desired plant species by a variety of conventional techniques. For reviews of such techniques see, for example, Weissbach & Weissbach Methods for Plant Molecular Biology (1988, Academic Press, N.Y.) Section VIII, pp. 421-463; and Grierson & Corey, Plant Molecular Biology (1988, 2d Ed.), Blackie, London, Ch. 7-9.

A DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) Nature 327:70-73). Alternatively, the DNA construct can be introduced into the plant cell via nanoparticle transformation (see, e.g., US Patent Publication No. 20090104700, which is incorporated herein by reference in its entirety). Alternatively, the DNA constructs may be combined with suitable T-DNA border/flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al. (1984) Science 233:496-498, and Fraley et al. (1983) Proc. Nat'l. Acad. Sci. USA 80:4803.

In addition, gene transfer may be achieved using non-*Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, See, e.g., Chung et al. (2006) Trends Plant Sci. 11(1):1-4.

The virulence functions of the *Agrobacterium tumefaciens* host will direct the insertion of a T-strand containing the construct and adjacent marker into the plant cell DNA when the cell is infected by the bacteria using binary T DNA vector (Bevan (1984) Nuc. Acid Res. 12:8711-8721) or the co-cultivation procedure (Horsch et al. (1985) Science 227: 1229-1231). Generally, the *Agrobacterium* transformation system is used to engineer dicotyledonous plants (Bevan et al. (1982) Ann. Rev. Genet. 16:357-384; Rogers et al. (1986) Methods Enzymol. 118:627-641). The *Agrobacterium* transformation system may also be used to transform, as well as transfer, DNA to monocotyledonous plants and plant cells. See U.S. Pat. No. 5,591,616; Hernalsteen et al. (1984) EMBO J. 3:3039-3041; Hooykass-Van Slogteren et al. (1984) Nature 311:763-764; Grimsley et al. (1987) Nature 325:1677-179; Boulton et al. (1989) Plant Mol. Biol. 12:31-40; and Gould et al. (1991) Plant Physiol. 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) EMBO J. 3:2717-2722, Potrykus et al. (1985) Molec. Gen. Genet. 199:169-177; Fromm et al. (1985) Proc. Nat. Acad. Sci. USA 82:5824-5828; and Shimamoto (1989) Nature 338:274-276) and electroporation of plant tissues (D'Halluin et al. (1992) Plant Cell 4:1495-1505). Additional methods for plant cell transformation include microinjection, silicon carbide mediated DNA uptake (Kaeppler et al. (1990) Plant Cell Reporter 9:415-418), and microprojectile bombardment (see Klein et al. (1988) Proc. Nat. Acad. Sci. USA 85:4305-4309; and Gordon-Kamm et al. (1990) Plant Cell 2:603-618).

The disclosed methods and compositions can be used to insert exogenous sequences into a predetermined location such as the E32 locus. This is useful inasmuch as expression of an introduced transgene into the maize genome depends critically on its integration site. Accordingly, genes encoding herbicide tolerance, insect resistance, nutrients, antibiotics or therapeutic molecules can be inserted, by targeted recombination.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in Handbook of Plant Cell Culture, pp. 124-176, Macmillian Publishing Company, New York, 1983; and Binding, Regeneration of Plants, Plant Protoplasts, pp. 21-73, CRC Press, Boca Raton, 1985. Regeneration can also be obtained from plant callus, explants, organs, pollens, embryos or parts thereof. Such regeneration techniques are described generally in Klee et al. (1987) Ann. Rev. of Plant Phys. 38:467-486.

One skilled in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed maize cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed cells can also be identified by screening for the activities of any visible marker genes (e.g., the beta-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, 51 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 (aryloxyalkanoate dioxygenase; see WO 2005/107437) and PAT (phosphinothricin-N-acetyltransferase (PAT), EC 2.3.1.183) proteins using an ELISA assay is described in U.S. Patent Publication No. 20090093366 which is herein incorporated by reference in its entirety. The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Administration of effective amounts is by any of the routes normally used for introducing fusion proteins into ultimate contact with the plant cell to be treated. The ZFPs are administered in any suitable manner, preferably with acceptable carriers. Suitable methods of administering such modulators are available and well known to those of skill in the art, and, although more than one route can be used to administer a particular composition, a particular route can often provide a more immediate and more effective reaction than another route.

EXAMPLES

Example 1: Production of Zinc Finger Proteins Designed to Bind the Genomic Locus for Corn Event DAS-59132

Zinc finger proteins directed against DNA sequences which comprise the genomic locus for Corn Event DAS-59132 (see, FIG. 1) were designed per the methods described in Urnov et al. (2005) Nature 435:646-651. Exemplary target sequence and recognition helices are shown in Table 1A (recognition helix regions designs) and Table 1B (target sites). In Table 1B, nucleotides in the target site that are contacted by the ZFP recognition helices are indicated in uppercase letters; non-contacted nucleotides are indicated in lowercase.

TABLE 1A

Genomic locus for Corn Event DAS-59132-binding zinc finger designs.

| ZFP# | F1 | F2 | F3 | F4 | F5 |
|---|---|---|---|---|---|
| 25716 | RSDDLSK SEQ ID NO: 43 | QSGSLTR SEQ ID NO: 44 | RSDNLRE SEQ ID NO: 45 | QSGDLTR SEQ ID NO: 46 | DTGARLK SEQ ID NO: 47 |
| 25717 | RSADRKT SEQ ID NO: 48 | DRSHLSR SEQ ID NO: 49 | TSGNLTR SEQ ID NO: 50 | RSDDLSR SEQ ID NO: 51 | QSANRTK SEQ ID NO: 52 |

TABLE 1B

Target Sequences for zinc finger proteins.

| Zinc Finger Number | SEQ ID NO: | Target Sequence |
|---|---|---|
| 25686 | 2 | caCAACAAGACtGCGGGTtcggtggcgc |
| 25687 | 3 | gaTAGGTGGCAGTGGCAgtggcactggc |
| 25688 | 4 | taTCGGCACAACAAGACtgcgggttcgg |
| 25689 | 5 | tgGCAGTGGCAGTGGCActggcacggca |
| 25692 | 6 | caGCAGATGAGcGGAGCGatcgatcgcg |
| 25693 | 7 | caGTGGATAGAGCAGCGttggccgttgg |
| 25710 | 8 | agGAAGCCGGCGGTGAAtgtcgccgtgt |
| 25711 | 9 | cgTCGCCAcTCGGCACAAggctcatcag |
| 25712 | 10 | atCGGGCATCGGCGACTgatgagccttg |
| 25713 | 11 | gaTCAACGGAAGCGGATGGCccgcttct |
| 25716 | 12 | tgATCGCAtCGGGCATCGgcgactgatg |
| 25717 | 13 | cgGAAGCGGATGGCCCGcttctttagaa |

The E32 zinc finger protein designs were incorporated into vectors encoding a protein having at least one finger with a CCHC structure. See, U.S. Patent Publication No. 2008/0182332. In particular, the last finger in each protein had a CCHC backbone for the recognition helix. The non-canonical zinc finger-encoding sequences were fused to the nuclease domain of the type IIS restriction enzyme FokI (amino acids 384-579 of the sequence of Wah et al. (1998) Proc. Natl. Acad. Sci. USA 95:10564-10569) via a four amino acid ZC linker and an opaque-2 nuclear localization signal derived from Zea mays to form Corn Event DAS-59132 zinc-finger nucleases (ZFNs). The optimal zinc fingers were verified for cleavage activity using a budding yeast based system previously shown to identify active nucleases. See, e.g., U.S. Patent Publication No. 20090111119; Doyon et al. (2008) Nat Biotechnol. 26:702-708; Geurts et al. (2009) Science 325:433. Zinc fingers for the various functional domains were selected for in-vivo use. Of the numerous ZFNs that were designed, produced and tested to bind to the putative Corn Event DAS-59132 genomic polynucleotide target sites, six pairs of ZFNs were identified as having in vivo activity at high levels, and selected for further experimentation. See, Table 1A. The selected ZFN pairs which optimally bound the E32 locus were advanced for testing in a transient corn transformation assay.

FIG. 1 shows the genomic organization of the E32 locus in relation to the ZFN polynucleotide binding/target sites of the six ZFN pairs. The first three ZFN pairs (E32 ZFN1, E32 ZFN2, and E32 ZFN3) bind upstream of the Corn Event DAS-59132 transgenic insert, the second three ZFN pairs (E32 ZFN4, E32 ZFN5, and E32 ZFN6) bind downstream of the Corn Event DAS-59132 transgenic insert. Four ZFNs were characterized as being capable of efficiently binding and cleaving Corn Event DAS-59132 genomic polynucleotide target sites in planta.

Example 2: Zinc Finger Nuclease Constructs and AAD-1 Gene Donor Construct

Plasmid vectors containing ZFN expression constructs of the six exemplary zinc finger nucleases were designed and constructed using skill commonly practiced in the art. Each zinc finger-encoding sequence was fused to a sequence encoding an opaque-2 nuclear localization signal (Maddaloni et al. (1989) Nuc. Acids Res. 17(18):7532), that was positioned upstream of the zinc finger nuclease.

The opaque-2 nuclear localization signal and zinc finger nuclease fusion sequence was paired with the complementary opaque-2 nuclear localization signal and zinc finger nuclease fusion sequence. As such, each construct consisted of a single open reading frame comprised of two opaque-2 nuclear localization signals and zinc finger nuclease fusion sequences separated by the 2A sequence from *Thosea asigna* virus (Mattion et al. (1996) *J. Virol.* 70:8124-8127). Expression of the ZFN coding sequence was driven by the highly expressing constitutive *Zea mays* Ubiquitin 1 promoter (Christensen et al. (1992) Plant Mol. Biol. 18(4):675-89) and flanked by the *Zea mays* Per 5 3' polyA untranslated region (U.S. Pat. No. 6,699,984). The resulting six plasmid constructs were confirmed via restriction enzyme digestion and via DNA sequencing. FIGS. 2 and 3 provide a graphical representation of the completed plasmid constructs. The ZFN expressed in plasmid construct, pDAB105906 (FIG. 2), contains "Fok-Mono" which is a wild type FokI endonuclease. The ZFN expressed in plasmid construct, pDAB111809 (FIG. 3), contains "Fok1-ELD" which is a modified Fold endonuclease. The modified Fok1 endonuclease contains alterations as described in Doyon Y., Vo T., Mendel M., Greenberg S., Wang J., Xia D., Miller J., Urnov F., Gregory P., and Holmes M. (2010) Enhancing zincfinger-nuclease activity with improved obligate heterodimeric architecture. *Nature Methods*, 8(1); 74-79.

A donor construct was designed to integrate into the ZFN cleaved genomic DNA of the E32 locus. FIG. 4 illustrates the donor construct, pDAB100655, which consists of a single gene expression cassette. This single gene expression cassette is comprised of the *Zea mays* Ubiquitin 1 promoter (ZmUbi1 promoter), the AAD-1 coding sequence (U.S. Pat. No. 7,838,733) and the *Zea mays* Per 5 3' untranslated region (ZmPer5 3' UTR). The construct contains a pair of repeated Corn Event DAS-59132 ZFN6 binding sequences which were included downstream of the AAD-1 gene expression cassette. The various gene elements were assembled in a high copy number pUC based plasmid.

Example 3: Transient Transformation of Maize Hi-II Cultures to Determine ZFN Efficiency Transformation of ZFN Genes Maize Hi-II embryogenic cultures were produced as described in U.S. Pat. No. 7,179,902 and were used to evaluate and test the efficiencies of the different ZFNs. Plasmid DNA consisting of pDAB105901, pDAB105902, pDAB105903, pDAB105904, pDAB105905 and pDAB105906 were transiently transformed into maize callus cells to compare the cutting frequency of different ZFNs against a standard tested ZFN, pDAB7430, which was designed to the inositol polyphosphate 2-kinase gene locus within the maize genome as described in U.S. Patent Application No. 2011/0119786.

From Hi-II cultures, 12 mL of packed cell volume (PCV) from a previously cryo-preserved cell line plus 28 mL of conditioned medium was subcultured into 80 mL of GN6 liquid medium (N6 medium (Chu et al., (1975) Sci Sin. 18:659-668), 2.0 mg/L 2, 4-D, 30 g/L sucrose, pH 6.0) in a 500 mL Erlenmeyer flask, and placed on a shaker at 125 rpm at 28° C. This step was repeated two times using the same cell line, such that a total of 36 mL PCV was distributed across three flasks. After 24 hours, the contents were poured into a sterile PETRI™ dish and the GN6 liquid media was removed. Slightly moistened callus was transferred to a 2.5 cm diameter circle on GN6 S/M solid medium (N6 Medium (Chu et al., (1975) Sci Sin. 18:659-668), 2.0 mg/L 2,4-D, 30 g/L sucrose, 45.5 g/L sorbitol, 45.5 g/L mannitol, 100 mg/L myo-inositol, 2.5 g/L Gelrite™, pH 6.0) containing filter paper. The plates were incubated in the dark for 4 hours at 28° C.

Microparticle gold (0.6 micron, BioRad, Hercules, Calif.,) was prepared for DNA precipitation by weighing out 21 mg into a sterile, siliconized 1.7 mL microcentrifuge tube (Sigma-Aldrich, St. Louis, Mo.) and 350 µL of ice cold 100% ethanol was added and vortexed for 1 minute. The gold was pelleted by centrifugation at 10,000 rpm for 15 seconds using a MINISPIN™ centrifuge (Eppendorf, Hauppauge, N.Y.). After removing the supernatant, 350 µL of ice cold, sterile water was added, mixed up and down with the pipette and centrifuged at 10,000 rpm for 15 seconds. The wash step was repeated one more time prior to suspending the gold in 350 µL of ice cold, sterile water. The washed gold was then stored at −20° C. until needed.

For each DNA precipitation, 3 mg of gold in 50 µL of water was aliqouted into a siliconized 1.7 mL microcentrifuge tube (Sigma-Aldrich, St. Louis, Mo.). Plasmid DNA (2.5 µg E32 ZFN in plasmids pDAB105901, pDAB105902, pDAB105903, pDAB105904, pDAB105905 or pDAB105906 and 2.5 µg IPK1 ZFN in plasmid pDAB7430) was premixed in 0.6 mL microcentrifuge tubes (Fisher Scientific, Nazareth, Pa.) and added to the gold suspension gently pipetting up and down 5-10 times to mix thoroughly. Twenty microliters (20 µL) of cold 0.1 M spermidine was then added and gently mixed by pipetting up and down 5-10 times. Fifty microliters (50 µL) of ice cold 2.5 M calcium chloride was added slowly and gently mixed by pipetting up and down 5-10 times. The tube was then capped and allowed to incubate at room temperature for 10 minutes. After centrifuging for 15 seconds at 10,000 rpm, the supernatant was carefully removed and 60 µL of ice cold, 100% ethanol was added. The gold DNA mixture was resuspended by gently pipetting up and down 5-10 times.

For microparticle bombardment, sterilized macrocarriers (BioRad, Hercules, Calif.) were fit into stainless steel holders (BioRad, Hercules, Calif.) and autoclaved. Nine microliters (9 µL) of gold/DNA suspension was evenly spread in the center of the macrocarrier being sure to pipette up and down so as to keep the suspension well mixed between aliquots. Macrocarriers were then placed onto a piece of sterile 125 mm Whatman #4 filter paper (GE Healthcare, Buckinghamshire, UK) on a bed of 8-mesh DRIERITE™ (W. A Hammond Drierite Co., Xenia, Ohio) in a 140×25 mm glass PETRI™ dish. The gold/DNA was allowed to dry completely for about 5-10 minutes. Rupture discs (1,100 psi, BioRad, Hercules, Calif.) were sterilized by soaking for a few seconds in isopropyl alcohol then loaded into the retaining cap of a microparticle bombardment devise (PDS-1000, BioRad, Hercules, Calif.). An autoclaved stopping screen (BioRad, Hercules, Calif.) and a loaded macrocarrier was placed into the launch assembly, the lid was screwed on and placed into the bombardment chamber just under the nozzle. The PETRI™ dish containing target was uncovered and placed in the bombardment chamber 6 cm below the nozzle. A vacuum was pulled (−0.9 bar) and the devise was fired. The above described steps were repeated for each target blasted. Targets were incubated in dark at a temperature of 28° C. for 24 hours on the same blasting medium. Blasted cells were transferred to recovery GN6 solid recovery medium (N6 medium (Chu et al., (1975) Sci Sin. 18:659-668), 2.0 mg/L 2, 4-D, 30 g/L sucrose, 2.5 g/L Gelrite, pH 6.0) and incubated for additional 48 hours at 28° C. in the dark. Seventy-two hours post bombardment, the cells were harvested into 2 mL EPPENDORF MICROFUGE SAFE LOCK TUBES™ and lyophilized for 48 hours in a VIRTIS MODEL #50L VIRTUAL XL-70 LYOPHILIZER™ (SP Scientific, Gardiner N.Y.).

Next Generation Sequencing (NGS) Analysis of Transiently Transformed Maize

The transiently transformed maize callus tissue was analyzed to determine the cleavage efficiency of the zinc finger nuclease proteins.

Sample Preparation

Maize callus tissue transiently transformed with the ZFN constructs and two control vectors, pDAB100664 and pDAB100665 were collected in 2 mL EPPENDORF™ tubes and lyophilized for 48 hr. Genomic DNA (gDNA) was extracted from lyophilized tissue using the QIAGEN PLANT DNA EXTRACTION KIT™ (Valencia, Calif.) according to manufacturer's specifications. The isolated gDNA was resuspended in 200 µL of water and the concentration was determined using a NANODROP® spectrophotometer (Invitrogen, Carlsbad, Calif.). Integrity of the DNA was estimated by running samples on a 0.8% agarose E-gels (Invitrogen). gDNA samples were normalized (25 ng/µL) for PCR amplification to generate amplicons which would be analyzed via ILLUMINA™ sequencing (San Diego, Calif.).

PCR primers for amplification of the genomic regions which span each tested ZFN cleavage site and the control samples were purchased from Integrated DNA Technologies (Coralville, Iowa). Optimum amplification conditions for the primers were identified by temperature gradient PCR using 0.2 µM appropriate primers, ACCUPRIME PFX SUPERMIX™ (1.1×, Invitrogen) and 100 ng of template genomic DNA in a 23.5 µL reaction. Cycling parameters were initial denaturation at 95° C. (5 min) followed by 35 cycles of denaturation (95° C., 15 sec), annealing (55-72° C., 30 sec), extension (68° C., 1 min) and a final extension (72° C., 7 min). Amplification products were analyzed on 3.5% TAE agarose gels. After identifying an optimum annealing temperature, preparative PCR reactions were carried out to validate each set of PCR primers and for generating the ILLUMINA™ sequencing amplicon.

For preparative PCR, 8-individual small scale PCR reactions were performed for each template using conditions described above and the resulting PCR products were pooled together and gel purified on 3.5% agarose gels using the QIAGEN MINELUTE GEL EXTRACTION/PURIFICATION KIT™ per manufacturer's recommendations. Concentrations of the gel purified amplicons were determined by NANODROP™ and the ILLUMINA™ sequencing samples were prepared by pooling approximately 100 ng of PCR amplicons from ZFN targeted and corresponding wild type controls. Primers used for the PCR amplicon generation are shown in Table 2 below.

TABLE 2

Oligonucleotides for amplification of ZFN binding sites.

| Corn Event DAS-59132 Zinc Finger Number | Direction//SEQ ID NO: | Primer Sequence |
|---|---|---|
| 25686/25687 and 25688/25689 | Forward//SEQ ID NO: 14 | CAGGCAGCGCCACCGAAC |
| | Reverse//SEQ ID NO: 15 | CGATCGATCGCGTGCCGT |
| 256892/256893 | Forward//SEQ ID NO: 16 | CTGGCACGGCACGCGATC |
| | Reverse//SEQ ID NO: 17 | CGGAGATCCGGCCCCAAC |
| 25710/25711 | Forward//SEQ ID NO: 18 | GACACGGCACACACGGCG |
| | Reverse//SEQ ID NO: 19 | TCGGGCATCGGCGACTGA |
| 25712/25713 and 25716/25717 | Forward//SEQ ID NO: 20 | ACTCGGCACAAGGCTCAT |
| | Reverse//SEQ ID NO: 21 | CCTGTGCCAATTCTAAAG |
| 9149/9215 | Forward//SEQ ID NO: 22 | GCAGTGCATGTTATGAGC |
| | Reverse//SEQ ID NO: 23 | CAGGACATAAATGAACTGAATC |

ILLUMINA™ Sequencing and Analysis

The ZFNs were designed to recognize, bind and modify specific DNA sequences within the genomic locus of transgenic Corn Event DAS-59132. The efficiency by which the six ZFNs cleaved the genomic locus were assayed to determine which ZFN cleaved most efficiently. ILLUMINA™ sequencing was performed at Cofactor Genomics (St. Louis, Mo.) and sequences were analyzed using a sequence analysis script. Low quality sequences were filtered out and the remaining sequences were parsed according to unique DNA sequences identifiers. The unique DNA sequences identifiers were then aligned with the reference sequence and scored for insertions/deletions (indels). To determine the level of cleavage activity, the region surrounding the ZFN cleavage site was scored for the presence of sequence variants which resulted from the indels. Cleavage activity for each ZFN in the study was calculated as the number of sequences with indels/1M high quality sequences or as a percentage of high quality sequences with indels. The levels of cleavage efficiency were determined by normalizing the ZFN level of cleavage activity with the activity of a ZFN directed to the IPP2-K gene as described in U.S. Patent Publication No. 2011/0119786.

The E32 ZFN6 which contains the 25716 and 25717 zinc finger binding domains cleaved the genomic locus of transgenic Corn Event DAS-59132 with the highest efficiency. This ZFN functioned at 3.8 times the efficiency of the control IPPK2 zinc finger nuclease. Given the high levels of cleavage activity of E32 ZFN6, this ZFN was selected for use in integrating the donor DNA fragment into the genomic locus via non homologous end-joining.

TABLE 3

Cleavage efficiency of the tested eZFNs.

| E32 ZFN Number | % IPPK2 ZFN Activity |
|---|---|
| 25686/25687 | 32 |
| 25688/25689 | 108 |
| 25712/25713 | 69 |
| 25716/25717 | 380 |

Example 4: Transient Expression of E32 ZFNs in Maize Protoplasts to Demonstrate NHEJ Targeting to the E32 Locus A rapid testing system for gene targeting was established to target the endogenous genomic loci of Corn Event DAS-59132 and to optimize donor targeting parameters in maize. Double strand breaks were generated within the genome at Corn Event DAS-59132 and repaired by either the non-homologous end joining (NHEJ) or homology dependent repair (HDR).

Protoplast Isolation

Maize Hi-II embryogenic suspension cultures were maintained on a 3.5 day subculturing schedule. A 10 mL solution of sterile 6% (w/v) cellulase and a 10 mL solution of sterile 0.6% (w/v) pectolyase enzyme solutions was pipetted into a 50 mL conical tube. Next, 4 mL of pack cell volumes (PCV) of Hi-II suspension cells were added into the 50 mL tube containing the digest solution and wrapped with Parafilm®. The tubes were placed on a platform rocker at room temperature for about 16-18 hr. Next, the cells and enzyme solution were slowly filtered through a 100 µM cell strainer placed in a 50 mL conical tube. The cells were then rinsed using a 100 µM cell strainer by pipetting 10 mL of W5 media through the strainer. The cells and enzyme solution were slowly filtered through a 70 µM cell strainer. This straining step was followed by another straining step, wherein the cells and enzyme solution were slowly filtered through a 40 µM cell strainer placed in a 50 mL conical tube. Using a 10 mL pipette tip, the 40 µM cell strainer was rinsed with 10 mL of W5 media to give a final volume of 40 mL and the tube was inverted. Very slowly, 8 mL of a sucrose cushion solution was added to the bottom of the protoplast/enzyme solution. Using a centrifuge with a swing arm bucket rotor, the tubes were spun for 15 minutes at 1,500 rpm. The protoplast cells were removed using a 5 mL narrow bore pipette tip. These cells (7-8 mLs) which were observed as a protoplast band were removed very slowly and put into a sterile 50 mL conical tube. Next, 25 mL of W5 media was used to wash the tubes. The W5 wash media was added to the protoplasts and the tubes were inverted slowly and centrifuged for 10 minutes at 1,500 rpm. The supernatant was removed and 10 mL of MMG solution was added with slow inversion of the tube to resuspend the protoplast pellet. The density of protoplasts were determined using a haemocytometer. Four PCVs yield about 30 million protoplasts.

Protoplast Transformation

The protoplast cells were diluted to 1.6 million protoplasts per mL using MMG solution. The protoplasts were gently resuspended by slowly inverting the tube. Next, 300 µL of protoplasts (about 500 k protoplasts) were added to a sterile 2 mL tube and the tubes were inverted to evenly distribute the protoplast cells. Plasmid DNA at a concentration of 40-80 µg in TE buffer was added to the protoplasts. The experimental conditions are described in Table 4. The tubes were slowly rolled to suspend the DNA with the protoplasts and the tubes were incubated for 5-10 minutes at room temperature. Next, 300 µL of a PEG solution was added to the protoplast/DNA solution. Once all the PEG solution had been added, the PEG solution was mixed with the protoplast solution by gently inverting the tube. The cocktail was incubated at room temperature for 15-20 minutes with periodic inverting of the tube(s). After the incubation, 1 mL of W5 solution was slowly added to the tubes and the tubes were gently inverted. Finally, the solution was centrifuged at 1,000 rpm for 15 minutes. The supernatant was carefully removed so as not to disturb the cell pellet. One milliliter of washing/incubating solution was added. The tubes were gently inverted to resuspend the cell pellet. The tubes were covered with aluminum foil to eliminate any exposure to light, and were laid on a rack on their side to incubate overnight. The cells were harvested 24 hours post-transformation for molecular analysis.

Sequence Validation of Targeting Using NGS

ZFN cleavage activity in maize protoplasts was determined using the Next Generation Sequencing method described in EXAMPLE 3. The sequenced PCR amplified fragments were scored for the presence of sequence variants resulting from indels. The relative frequency of indels from each of E32 ZFN6 treatment cleaved the genomic locus of transgenic Corn Event DAS-59132 at about 1.5% of the DNA molecules in the amplicons.

Demonstration of Targeting Using In-Out PCR

Targeting of an AAD-1 gene-containing donor cassette into the genomic locus of transgenic Corn Event DAS-59132 into the Hi-II maize transgenic cell suspensions via NHEJ was confirmed via a in-out PCR reactions. The in-out PCR reactions amplified fragments containing the junction of the AAD-1gene donor and genomic locus of transgenic Corn Event DAS-59132. The resulting amplicon was subjected to a second PCR reaction, wherein primers were designed to bind internally within the first amplicon. The combination of two independent PCR reactions resulted in the removal of background amplifications which may be false-positives.

The in-out PCR results of the protoplast transformation experiments demonstrated that the genomic locus of transgenic Corn Event DAS-59132 could be reproducibly targeted with a 5.3 kb AAD-1gene plasmid donor and the E32-ZFN6 zinc finger nuclease at a ratio of 1:10 µg of DNA Targeting via a NHEJ method was evidenced by the insertion of the AAD-1gene donor cassette in both orientations. Sequence of the in-out PCR amplicons showed three instances of perfect integration of the donor DNA.

Example 5: WHISKERS™ Mediated Stable Transformation of ZFN and Donor for Targeted Integration Via NHEJ in Maize Hi-II Cultures Transgenic events were targeted to the endogenous genomic locus of Corn Event DAS-59132. Constructs as

TABLE 4

Treatment groups for protoplast transformation.

| Treatment Groups | Donor DNA pDAB100651 (µg) | E32-ZFN6 pDAB105906 (µg) | pUC19 Filler (µg) | Salmon Sperm DNA Filler (µg) | Total DNA (µg) |
|---|---|---|---|---|---|
| E32 Donor alone + No enzyme control (filler-1) | pDAB100651 (40 µg) | N/A (0 µg) | pUC19 (40 µg) | N/A (0 µg) | 80 |
| E32 Donor alone + No enzyme control (filler-2) | pDAB100651 (40 µg) | N/A (0 µg) | N/A (0 µg) | ssDNA (40 µg) | 80 |
| E32 Donor alone control (no filler) | pDAB100651 (40 µg) | N/A (0 µg) | N/A (0 µg) | N/A (0 µg) | 40 |
| E32-ZFN6 alone control (no donor) filler1 | N/A (0 µg) | pDAB105906 (4 µg) | pUC19 (76 µg) | N/A (0 µg) | 80 |
| E32-ZFN6 alone control (no donor) filler2 | N/A (0 µg) | pDAB105906 (4 µg) | N/A (0 µg) | ssDNA (76 µg) | 80 |
| E32-ZFN6 wt FokI alone control (no donor) No filler | N/A (0 µg) | pDAB105906 (40 µg) | N/A (0 µg) | N/A (0 µg) | 40 |
| E32-ZFN6 wt FokI + E32 Donor (1:10) filler1 | pDAB100651 (40 µg) | pDAB105906 (4 µg) | pUC19 (36 µg) | N/A (0 µg) | 80 |
| E32-ZFN6 wt FokI + E32 Donor (1:10) filler2 | pDAB100651 (40 µg) | pDAB105906 (4 µg) | N/A (0 µg) | ssDNA (36 µg) | 80 | described in Example 1 include the donor sequence (pDAB100655) and Event 32 ZFN 6 (E32 ZFN6; pDAB105906).

Maize callus cells, consisting of 12 mL of packed cell volume (PCV) from a previously cryo-preserved Hi-II cell line, plus 28 mL of conditioned medium was subcultured into 80 mL of GN6 liquid medium (N6 medium (Chu et al., (1975) Sci Sin. 18:659-668), 2.0 mg/L of 2, 4-D, 30 g/L sucrose, pH 5.8) in a 500 mL Erlenmeyer flask, and placed on a shaker at 125 rpm at 28° C. This step was repeated two times using the same cell line, such that a total of 36 mL PCV was distributed across three flasks. After 24 hours, the GN6 liquid media was removed and replaced with 72 mL GN6 S/M osmotic medium (N6 Medium, 2.0 mg/L 2,4-D, 30 g/L sucrose, 45.5 g/L sorbitol, 45.5 g/L mannitol, 100 mg/L myo-inositol, pH 6.0). The flask was incubated in the dark for 30-35 minutes at 28° C. with moderate agitation (125 rpm). During the incubation period, a 50 mg/mL suspension of silicon carbide WHISKERS™ (Advanced Composite Materials, LLC, Greer, S.C.) was prepared by adding 8.1 mL of GN6 S/M liquid medium to 405 mg of sterile, silicon carbide WHISKERS™.

Following incubation in GN6 S/M osmotic medium, the contents of each flask were pooled into a 250 mL centrifuge bottle. After all cells in the flask settled to the bottom, the content volume in excess of approximately 14 mL of GN6 S/M liquid was drawn off and collected in a sterile 1 L flask for future use. The pre-wetted suspension of WHISKERS™ was mixed at maximum speed on a vortex for 60 seconds, and then added to the centrifuge bottle.

In this example, 159 μg of pDAB100655 (donor sequence) and 11 μg of pDAB10506 (ZFN) plasmid DNA were added to each bottle. Once the plasmid DNA was added, the bottle was immediately placed in a modified RED DEVIL 5400™ commercial paint mixer (Red Devil Equipment Co., Plymouth, Minn.), and agitated for 10 seconds. Following agitation, the cocktail of cells, media, WHISKERS™ and plasmid DNA were added to the contents of a 1 L flask along with 125 mL fresh GN6 liquid medium to reduce the osmoticant. The cells were allowed to recover on a shaker set at 125 rpm for 2 hours. About 6 mL of dispersed suspension was filtered onto Whatman #4 filter paper (5.5 cm) using a glass cell collector unit connected to a house vacuum line such that 60 filters were obtained per bottle. Filters were placed onto 60×20 mm plates of GN6 solid medium (same as GN6 liquid medium except with 2.5 g/L glufosinate).

Identification and Isolation of Putative Targeted Events

One week post-DNA delivery, filter papers were transferred to 60×20 mm plates of GN6 (1H) selection medium (N6 Medium, 2.0 mg/L 2, 4-D, 30 g/L sucrose, 100 mg/L myo-inositol, 2.5 g/L Gelrite, pH 5.8) containing a selective agent. These selection plates were incubated at 28° C. for one week in the dark. Following 1 week of selection in the dark, the tissue was embedded onto fresh media by scraping ½ the cells from each plate into a tube containing 3.0 mL of GN6 agarose medium held at 37-38° C. (N6 medium, 2.0 mg/L 2, 4-D, 30 g/L sucrose, 100 mg/L myo-inositol, 7 g/L SEAPLAQUE® agarose, pH 5.8, autoclaved for 10 minutes at 121° C.).

The agarose/tissue mixture was broken up with a spatula, and then 3 mL of agarose/tissue mixture was evenly poured onto the surface of a 100×25 mm PETRI™ dish containing GN6 (1H) medium. This process was repeated for both halves of each plate. Once all the tissue was embedded, the plates were incubated at 28° C. under dark conditions for up to 10 weeks. Putatively transformed isolates that grew under these selection conditions were removed from the embedded plates and transferred to fresh selection medium in 60×20 mm plates. If sustained growth was evident after approximately 2 weeks, an event was deemed to be resistant to the applied herbicide (selective agent) and an aliquot of cells was subsequently harvested for genotype analysis. In this example, 24 events were recovered from 6 treated bottles. These events were advance for molecular analysis to confirm the integration.

Molecular Analysis of NHEJ Targeting to the E32 Locus

The 24 events that were recovered from the WHISKERS™ mediated transformation, as described above, were analyzed using several different molecular tools. As a result of the analysis, events which contained a copy of the AAD-1 transgene integrated within the E32 genomic locus were identified. The 24 various events were confirmed to contain a copy of the AAD-1 transgene and then it was determined if there was disruption of the E32 site by either indels or by the insertion of AAD-1 cassette. The events that were positive for the presence of the AAD-1 gene and a disrupted ZFN site were further characterized for the presence of the expected donor and target junction fragments (by In-Out PCR), and for expected molecular weight fragments that corresponded with band sizes in Southern blot that indicated a targeted insertion of the donor DNA region within the E33 genomic locus. These assays confirmed that events containing a copy of the AAD-1 transgene integrated within the E32 genomic locus via an NHEJ mechanism.

DNA Extraction

DNA was extracted from lyophilized maize callus tissue using a QIAGEN BIOSPRINIT 96™ DNA isolation kit per manufacturer's recommendations. A pre-defined program was used for the automation extraction and DNA was eluted in 200 μL of 1:1 TE Buffer/distilled water. Two microliters (2 μL) of each sample was quantified on THERMOSCIENTIFIC NANODROP 8000™ and samples were normalized to 100 ng/μL using QIAGEN BIOROBOT 3000™. Normalized DNA was stored at 4° C. until further analysis.

Copy Number Evaluation

Transgene copy number determination by a hydrolysis probe assay, analogous to a TAQMAN® assay, was performed by real-time PCR using the LIGHTCYCLER®480 system (Roche Applied Science, Indianapolis, Ind.). Assays were designed for AAD-1 and the internal reference gene, Invertase, using LIGHTCYCLER® Probe Design Software 2.0. For amplification, LIGHTCYCLER®480 Probes Master mix (Roche Applied Science, Indianapolis, Ind.) was prepared at 1× final concentration in a 10 μL volume multiplex reaction containing 0.4 μM of each primer and 0.2 μM of each probe (Table 5). A two step amplification reaction was performed with an extension at 60° C. for 40 seconds with fluorescence acquisition. Analysis of real time PCR copy number data was performed using LIGHTCYCLER® software release 1.5 using the relative quant module and is based on the ΔΔCt method. For this, a sample of gDNA from a single copy calibrator and a known two-copy check were included in each run.

TABLE 5

Primer/Probe Sequences for hydrolysis probe assay of AAD-1 and internal reference.

| Primer Name | Sequence | Detection |
|---|---|---|
| GAAD1F | SEQ ID NO: 24; TGTTCGGTTCCCTCTACCAA | — |

TABLE 5-continued

Primer/Probe Sequences for hydrolysis probe assay of AAD-1 and internal reference.

| Primer Name | Sequence | Detection |
|---|---|---|
| GAAD1R | SEQ ID NO: 25; CAACATCCATCACCTTGACTGA | — |
| GAAD1R | SEQ ID NO: 26; CACAGAACCGTCGCTTCAGCAACA | FAM |
| IVF-Taq | SEQ ID NO: 27; TGGCGGACGACGACTTGT | — |
| IVR-Taq | SEQ ID NO: 28; AAAGTTTGGAGGCTGCCGT | — |
| IV-Probe | SEQ ID NO: 29; CGAGCAGACCGCCGTGTACTTCTACC | HEX |

Corn Event DAS-59132 Genomic Locus Disruption Assay

A genomic locus disruption assay for Corn Event DAS-59132 was performed by real-time PCR using the LIGHTCYCLER®480 system (Roche Applied Science, Indianapolis, Ind.). Assays were designed to monitor the specificity for which E32 ZFN6 (25716/25717) bound and cleaved genomic sequences of the E32 locus and the internal reference gene invertase using the LIGHTCYCLER® Probe Design Software 2.0. For amplification, LIGHTCYCLER®480 Probes Master mix (Roche Applied Science, Indianapolis, Ind.) was prepared at 1× final concentration in a 10 µL volume multiplex reaction containing 0.4 µM of each primer and 0.2 µM of each probe (Table 6). A two step amplification reaction was performed with an extension at 55° C. for 30 seconds with fluorescence acquisition. Analysis for the disruption assay was performed using target to reference ratio (FIG. 5). Four of the eight events were identified as containing an AAD-1 transgene integrated into the genomic locus of Corn Event DAS-59132. The following events, consisting of; Event 100655/105906[1]-001, Event 100655/105906[5]-013, Event 100655/105906[5]-015, and Event 100655/105906[3]-018, were advance for further molecular analysis to confirm the integration of the AAD-1 transgene within the genomic locus of Corn Event DAS-59132.

Event32 Locus Specific In-Out qPCR

The insertion of the AAD-1 donor DNA within the genomic locus of E32 via NHEJ can occur in one of two orientations. The integration of the AAD-1 transgene and the orientation fo the insert were confirmed with an in-out PCR assay. The in-out PCR assay utilizes an "out" primer that was designed to bind to the genomic locus of E32; an "in" primer was designed to bind to the AAD-1 donor sequence. The amplification reactions using these primers only amplify a donor gene which is inserted at the target site. The resulting PCR amplicons represent the junction fragments of the E32 target site and the donor DNA sequences at either the 5' or 3' ends of the insert. Positive and negative controls were included in the assay. Two positive control plasmids, pDAB100664 and pDAB100665, were constructed to simulate donor insertion at the genomic locus of E32 in each of the two different orientations.

For the in-out PCR, a DNA intercalating dye, SYTO-13®, was used in the PCR mix in order to detect amplification in real time on a thermocycler with fluorescence detection capability. In addition, a melting temperature (Tm) analysis program was attached to a regular PCR program so the amplified products could be analyzed for their Tm profiles. Any similarity between the Tm profiles of an unknown sample and the positive control sample would indicate that the unknown sample has the same amplified product as that of the positive control. The PCR reactions were conducted using 10 ng of template genomic DNA, 0.2 µM dNTPs, 0.2 µM forward and reverse primers, 4 µM SYTO-13® and 0.15 µL of Ex Taq HS. Reactions were completed in two steps: the first step consisted of one cycle at 94° C. (2 minutes) and 35 cycles at 98° C. (12 seconds), 66° C. (30 seconds) and 68° C. (1.3 minutes); the second step was a Tm program covering 60-95° C. followed by 65° C. (30 seconds) and 72° C. (10 minutes) (Table 6). The amplicons were sequenced to confirm that the AAD-1 gene had integrated within the genomic locus of E32.

The results of the real-time, in-out PCR amplicons were visualized using the ABI software. These results were further confirmed using a gel shift assay, wherein the amplicons were run on a 1.2% TAE gel. Expected amplicon sizes were approximately 1.8 kb for the orientation as depicted in pDAB100664 and about 2 kb for the orientation depicted in pDAB100665. The gel shift assay results confirmed the real-time, in-out PCR data.

The locus disruption data and in-out PCR suggested that a copy of the AAD-1 transgene had integrated via NHEJ into the E32 locus in some maize events recovered by selection on 2,4-D.

TABLE 6

Primers for In-Out PCR to detect NHEJ mediated targeting.

| Primer Name | Sequence | Expected Amplicon size/control |
|---|---|---|
| E32-3R2 NJ-AAD1-Pri2 | Forward Primer SEQ ID NO: 30 GCC CTT ACA GTT CAT GGG CG Reverser Primer SEQ ID NO: 31 GAC CAA GTC CTT GTC TGG GAC A | 1.8 kb pDAB100664 |
| E32-5F1 NJ-AAD1-Pri2 | Forward Primer SEQ ID NO: 32 ACA AAC ACG TCC TCC AAG GCT Reverse Primer SEQ ID NO: 33 GAC CAA GTC CTT GTC TGG GAC A | 2.0 kb pDAB100665 |

Southern Blot Analysis

The maize callus events identified above as putatively targeted were further screened using a Southern blot assay to confirm that the AAD-1 transgene had integrated via NHEJ into the E32 locus. The Southern blot analysis experiments generated data which demonstrated the integration and integrity of the AAD-1 transgene within the maize genome.

DNA Extraction

Genomic DNA was extracted from the callus tissue harvested from each individual event. Initially, the tissue samples were collected in 2 mL tubes and lyophilized for 2 days. Tissue maceration was performed with a KLECO TISSUE PULVERIZER™ and tungsten beads (Kleco, Visalia, Calif.). Following tissue maceration the genomic DNA was isolated using the DNEASY PLANT MINI KIT™ (Qiagen, Germantown, Md.) according to the manufacturer's suggested protocol.

Genomic DNA (gDNA) was quantified using the QUANT-IT PICO GREEN DNA ASSAY KIT™ (Molecular Probes, Invitrogen, Carlsbad, Calif.). Quantified gDNA was adjusted to 4 μg for the Southern blot analysis. DNA samples were then digested using the NcoI restriction enzyme (New England BioLabs, Ipswich, Mass.) overnight at 37° C. and purified using QUICK-PRECIP™ (Edge BioSystem, Gaithersburg, Md.) according to the manufacturer's suggested protocol. DNA was resuspended in 1× dye and electrophoresed for 5 hours on a 0.8% SEAKEM LE AGAROSE™ (Lonza, Rockland, Me.) gel. The gel was denatured, neutralized, and then transferred to a nylon charged membrane (Millipore, Bedford, Mass.) overnight and DNA was crosslinked to the membrane using a UV STRATA LINKER 1800™ (Stratagene, La Jolla, Calif.), and blots were prehybridized with 20 mL of PERFECTHYB PLUS™ (Sigma, St. Louis, Mo.). The 226 bp probe SEQ ID NO:34 (GTGCATTCGGATTACTGTTTAGTCGAGTCATATTTAAGGAATTCATTGTAAATGTTCT AACCTAACCTAAGTATTAGGCAGCTATGGCTGATATGGATCTGATTGGACTTGA TTT ATCCATGATAAGTTTAAGAGCAACTCAAAGAGGTTAGGTATATATGGTTTTGTAAAG GTAAATTTAGTTAATATTAGAAAAAAAAAGTGTATCCAATAGGCTCTATAAACA) was labeled using PRIME-IT RMT RANDOM™ (Stratagene, La Jolla, Calif.) according to manufacturer's suggested protocol and purified using PROBE QUANT G-50 MICRO COLUMNS™ (GE Healthcare, Buckinghamshire, UK) per the manufacturer's suggested protocol. Approximately, 20×10⁶ cpm of the labeled probe was added to the blots and incubated overnight. Blots were washed twice for 15 minutes per wash and placed on a phosphor image screen for 24 hours and analyzed by a STORM 860 SCANNER™ (Molecular Dynamics).

The results from Southern blot analysis showed DNA from some events had NcoI bands of the size expected (2.9 and 5.5 kb) from integration of the donor DNA via NHEJ into the E32 locus.

The transformed maize tissue was regenerated into fertile corn plants bearing the true-breeding phenotype resistance to the 2,4-dichlorophenoxyacetic acid herbicides conferred by the AAD-1 gene introduced by the donor DNA.

Example 6: Targeting Event 32 Via Homology Directed Repair in Zea mays c.v. Hi-IIPlasmid Vectors Plasmid vectors containing ZFN expression constructs were constructed as described in Example 2. The ZFN expressed in plasmid construct, pDAB105906 (FIG. 2), contains "Fok-Mono" which is a wild type FokI endonuclease. The ZFN expressed in plasmid construct, pDAB111809 (FIG. 3), contains "Fok1-ELD" which is a modified Fold endonuclease. The modified Fok1 endonuclease contains alterations as described in Doyon Y., Vo T., Mendel M., Greenberg S., Wang J., Xia D., Miller J., Urnov F., Gregory P., and Holmes M. (2010) Enhancing zinc-finger-nuclease activity with improved obligate heterodimeric architecture. *Nature Methods*, 8(1); 74-79.

A donor construct, pDAB107855 (FIG. 15), was designed and built to integrate into the ZFN cleaved genomic DNA of the DAS-59132 genomic locus. This single gene expression cassette is comprised of the OsAct1 promoter, the phosphinothricin acetyl transferase (PAT) coding sequence:: and the ZmLip 3' UTR. In addition, the donor plasmid was designed with 1 kb sequences (homology arms) on either end of the target PAT gene that were homologous to sequence on either end of the ZFN cut site in the DAS-59132 genomic locus. The homology arms served as the substrate that the homologous recombination machinery used to insert the transgene into the genomic ZFN cut site. The various gene elements were assembled in a high copy number pUC based plasmid.

Plant Transformation

WHISKERS™ transformations were done as described in EXAMPLE 5 using pDAB107855 (donor sequence) and pDAB105906 (ZFN) plasmid DNA.

Molecular Analysis to Confirm Targeted Integration of a Pat Gene Cassette into the E32 Locus of Hi-II DNA Extraction DNA extractions were done as described in EXAMPLE 5.

Targeted Locus Disruption Assay

WHISKERS™ mediated transformation of Hi-II callus cells with the DAS-59132-ZFN and donor plasmid resulted in targeted and random transgene insertions. To distinguish random insertion events from the targeted event populations, all 854 events generated were initially screened using a locus disruption assay (done as described in EXAMPLE 5 using primers in Table 7). This assay determined whether the ZFN binding site within the locus remains intact or had been disrupted through ZFN cleavage or donor insertion. Indication of a disruption within the genomic loci is initial evidence that the ZFN has cleaved the endogenous DAS-59132 target locus and indicates targeted insertion of the donor DNA molecule. Primers were designed to amplify the endogenous target region that contains the ZFN recognition sites, and samples were set up to be analyzed by qPCR. Amplification of the intact region, indicative of an untargeted event, resulted in a 140 base pair amplicon measured as a detectable qPCR signal. Successful targeted integration of the donor molecule results in disruption of the detectable qPCR signal and is shown as a lower overall signal compared to control.

TABLE 7

Oligonucleotide Primer and Probe Sequences for targeted Locus Disruption Assay.

| Primer Name | SEQ ID NO: | Sequence | Detection |
|---|---|---|---|
| MAS604 | SEQ ID NO: 35 | ACACGGCACACACGGCGACATTCA | — |
| MAS606 | SEQ ID NO: 36 | AGGGCAGTGGCCAGTGTTCCTGTG | — |
| UPL 69 | — | Roche Sequence | FAM |
| IVF-Taq | SEQ ID NO: 37 | TGGCGGACGACGACTTGT | — |
| IVR-Taq | SEQ ID NO: 38 | AAAGTTTGGAGGCTGCCGT | — |
| IV-Probe | SEQ ID NO: 39 | CGAGCAGACCGCCGTGTACTTCTACC | HEX |

The 854 events generated from precision transformation were screened with the disruption assay, and scored as disrupted based on a significant drop in the target to reference signal. The results indicated that 63 of the 854 events assayed had a disrupted signal at the targeted locus, indicative of targeted gene insertion or indels at the site.

Targeted Locus In-Out PCR Assay

The presence of an insert were further confirmed using in-out PCR as described in EXAMPLE 5 and using the primers in Table 8. Positive samples identified on the real-time system were further confirmed using a standard gel shift assay.

TABLE 8

Primer and Probe Sequences for DAS-59132 Locus In-Out Assay.

| | Primer Name | SEQ ID NO: | Primer Sequence |
|---|---|---|---|
| 5' Junction Sequence | E32-5F3 | SEQ ID NO: 40 | GAAGGCAAAACGAATATAAGTGC ATTCGG |
| | E32-OLP-R1 | SEQ ID NO: 41 | TCGTGGATAGCACTTTGGGCT |
| 3' Junction Sequence | E32-OLP-F3 | SEQ ID NO: 42 | TCTACAGTGAACTTTAGGACAGA GCCA |
| | E32-3R2 | SEQ ID NO: 30 | GCCCTTACAGTTCATGGGCG |

The results of the disruption assay and the targeted locus in-out PCR assay were further confirmed via Southern blotting and sequencing (standard of Next Generation Sequencing).

In this example, 63 events out of a total of 854 samples submitted showed disruption of the E32 Locus. Of these, 8 targeted events were identified by in-out PCR and Southern analysis.

The transformed maize tissue was regenerated into fertile corn plants bearing the true-breeding phenotype, resistance to glufosinate and L-phosphinothricin, herbicides, of the donor DNA.

Example 7: Agrobacterium-Mediated Delivery of Plasmid Vectors for Event 32 Locus Disruption in Zea mays c.v. B104

Transformation

Zea mays c.v. B104 was transformed with binary constructs pDAB108688 (control vector, FIG. 6) and pDAB108690 (targeting vector, FIG. 7) using the superbinary transformation system (U.S. Pat. No. 5,591,616). As such, Agrobacterium was used for delivery of the ZFNs to the E32 genomic locus. Transgenic maize callus were obtained and analyzed via molecular confirmation assays to determine whether or not the E32 genomic locus of Zea mays c.v. B104 was disrupted. The results of the assays confirmed that Agrobacterium could be used to deliver ZFNs to cleave and disrupt the E32 genomic locus.

Binary Vectors

A binary construct, pDAB108690 (targeting vector, FIG. 7), was designed and built to contain a donor gene expression cassette and a ZFN gene expression cassette. This donor gene expression cassette was comprised of the Zea mays Ubiquitin 1 gene promoter (Zm Ubi1 promoter), the AAD-1 coding sequence and was terminated by the Zea mays lipase 3' untranslated region (ZmLip 3'UTR). In addition, the donor plasmid was designed with 1 kb sequence (homology arms) on either end of the AAD-1 gene that are homologous to sequence on either end of the ZFN cut site in the E32 genomic locus to facilitate donor insertion by HDR. The ZFN gene expression cassette was comprised of the rice Actin1 gene promoter (OsAct1 promoter), the 25716 and 25717 ZFN coding sequences and the ZmPer5 3' UTR.

In addition, a second control binary construct, pDAB108688 (control vector, FIG. 6), was designed and built to contain a gene expression cassette the same AAD-1 gene In addition, the donor plasmid was designed with 1 kb sequence (homology arms) on either end of the target aad-1 gene that is homologous to sequence on either end of the ZFN cut site in the E32 genomic locus.

Zea mays c.v. B104 Transformations

The constructs were transferred into Agrobacterium and used to transform Zea mays c.v. B104. The transformation procedure that was utilized is described in U.S. Pat. Pub. No. 2013/0157369. After completion of the transformation, isolated maize callus tissues were selected for and obtained from media containing the herbicide selectable agent. Table 9 shows the transformation frequency in the experiments. The resulting events were analyzed via molecular analysis to confirm ZFN mediated cleavage of the E32 Locus of Zea mays c.v. B104 following delivery of ZFN and donor via Agrobacterium-mediated transformation.

TABLE 9

Summary of transformation events produced using pDAB108688 (control vector) and pDAB108690 (targeting vector).

| Construct | Number of immature embryos transformed | Putative events produced | Transformation frequency (%) |
|---|---|---|---|
| pDAB108688 (control vector) | 930 | 355 | 38.17 |
| pDAB108690 (targeting vector) | 4789 | 1002 | 20.92 |

Genomic DNA Isolation for PCR from Callus Tissue

Genomic DNA was isolated as described in EXAMPLE 5.

Copy Number Determination

Transgene detection by hydrolysis probe assay, analogous to TaqMan® assay, was performed by real-time PCR using the LightCycler®480 system (Roche Applied Science). Assays were designed for detection of AAD-1 and ZFN disruption and were multiplexed with internal reference assays (Invertase) to ensure appropriate amount of gDNA was present in each assay. For amplification, LightCycler®480 Probes Master Mix™ (Roche Applied Science, Indianapolis, Ind.) was prepared at 1× final concentration in a 10 µL volume multiplex reaction containing 0.4 µM of each primer and 0.2 µM of each probe (Table 10). A two step amplification reaction was performed with an extension at 60° C. for 40 seconds (for the AAD1 reaction) or 60° C. for 30 seconds (for the ZFN disruption reaction) and with fluorescence acquisition.

Cp scores, the point at which the fluorescence signal crosses the background threshold using the fit points algorithm (Light Cycler® software release 1.5) and the Relative Quant module (based on the ΔΔCt method), was used to perform the analysis of real time PCR data.

The ZFN disruption qPCR assay determines if the ZFN target site is intact or has been modified during the experiment (by donor insertion or by NHEJ). This assay used the Roche UPL probe with primers designed to anneal outside of the ZFN cut site and probe hybridization region (FIG. 8). If events are disrupted at both alleles, the target to reference ratio is reduced compared to controls. Analysis of non-targeted controls and events that are not disrupted showed a target to reference ratio in the 0.4 to 0.6 range; disrupted events showed a target to reference ratio in the 0.2 to 0.35 range (FIG. 9).

This data demonstrates that the E32 Locus can be cleaved by introduction of the ZFN via Agrobacterium-mediated transformation.

TABLE 10

Primers and probes for qPCR.

| Name | SEQ ID NO: | Oligo Sequence | Probe (Flourophore/quencher) |
|---|---|---|---|
| MAS604 | SEQ ID NO: 53 | ACACGGCACACACGGCGACATTCA | — |
| MAS606 | SEQ ID NO: 54 | AGGGCAGTGGCCAGTGTTCCTGTG | — |
| UPL69 | — | See Roche | See Roche |
| IVF-Taq | SEQ ID NO: 55 | TGGCGGACGACGACTTGT | — |
| IVR-Taq | SEQ ID NO: 56 | AAAGTTTGGAGGCTGCCGT | — |
| IV-Probe | SEQ ID NO: 57 | CGAGCAGACCGCCGTGTACTTCTACC | HEX/BHQ |
| GAAD1F | SEQ ID NO: 58 | TGTTCGGTTCCCTCTACCAA | — |
| GAAD1R | SEQ ID NO: 59 | CAACATCCATCACCTTGACTGA | — |
| GAAD1P | SEQ ID NO: 60 | CACAGAACCGTCGCTTCAGCAACA | FAM |

Example 8: Event 32 Locus Targeting Via Homology Directed Repair in Zea mays c.v B104

Vectors

Plasmid vectors for expression of ZFNs were described in EXAMPLE 2.

A donor construct, pDAB104179 (FIG. 10, SEQ ID NO:61), designed to integrate into the ZFN cleaved genomic DNA of the E32 genomic locus was a single gene expression cassette comprised of the OsAct1 promoter, the PAT coding sequence and the ZmLip 3' UTR. In addition, the donor plasmid was designed with 1 kb sequence (homology arms) on either end of the target PAT gene that is identical to sequence on either end of the ZFN cut site in the E32 genomic locus to facilitate integration of the donor DNA region.

Transformation into B104 Using Particle Bombardment

Ears of the inbred line Zea mays c.v. B104 were self-pollinated and harvested when immature embryos were approximately 1.8-2.2 mm in length. De-husked ears were transported to the laboratory for sterilization. The end of a #4 stainless steel scalpel handle (lacking a blade) was placed into the distal portion of each ear. Ears were scrubbed with a nailbrush using liquid detergent (Liqui-Nox®, ALCONOX, Inc.) and surface-sterilized by immersion in 20% commercial bleach (Ultra Clorox® Germicidal Bleach, 6.15% sodium hypochlorite) for 20 minutes then rinsed with sterile deionized water 3 times inside a laminar flow hood. Immature zygotic embryos were aseptically excised from each ear and placed into an Eppendorf™ tube containing approximately 2.0 mL 'LS-inf medium' (LS salts, N6 vitamins, 68.5 g/L sucrose, 36 g/L D-glucose, 700 mg/L L-proline and 1.5 mg/L 2,4-D). The contents of the tube were poured onto plates of 'resting medium' (MS salts and vitamins, 30 g/L sucrose, 700 mg/L L-proline, 15 mg/L silver nitrate, 500 mg/L MES, 100 mg/L casein hydrolysate, 100 mg/L myo-inositol and 3.3 mg/L dicamba adjusted to pH 5.8 and solidified with 2.3 g/L Gelzan™), excess liquid was removed, and embryos were oriented with the scutellum facing upwards. Plates were placed at 28° C. with 24 hours continuous lighting at 50 µmoles/m²s for 3 days.

Four hours prior to bombardment, 30 embryos were arranged in the center of Petri dish of 'osmolysis medium' Cresting medium with the addition of 45.5 g/L sorbitol and 45.5 g/L mannitol) within a 2.5 cm diameter area with the scutella facing upwards. The embryos were incubated on this medium for 4 hours at 50 µmoles/m²s at 28° C. prior to bombardment.

To prepare gold microparticles for bombardment, 15 mg of 0.6 micron gold (Bio-Rad, Hercules, Calif., USA) were weighed into a siliconized microcentrifuge tube and 500 µL of cold ethanol (100%) was added. The tube was sonicated in an ultrasonic water bath for 15 seconds, allowed to sit at room temperature for 30 minutes, and then centrifuged for 60 seconds at 3,000 rpm. The supernatant was removed, and 1 mL cold, sterile water was added. The tube was finger-vortexed, allowed to settle for 3-5 minutes, and centrifuged for 60 seconds at 3,000 rpm. The supernatant was removed, and the water wash was repeated two additional times. After the second water wash, the gold was re-suspended in 500 µL cold water, sonicated for 15 seconds, and aliquoted 25 µL at a time into 10 sterile, siliconized microcentrifuge tubes. Individual tubes were frozen at −20° C. until use.

For precipitation of DNA onto prepared gold microparticles, one tube of gold was thawed for every 10 plates to be bombarded. The tube was sonicated in an ultrasonic water bath for 15 seconds, finger-vortexed, and then tapped on the laminar flow hood surface to gather all droplets to the bottom. To obtain a 20:1 molar ratio of donor to zinc finger constructs, 4.75 µg of donor DNA (pDAB104182) was pre-mixed with 0.25 µg of zinc finger (pDAB105941), then added to the gold, while pipetting up and down. Fifty µL of 2.5 M calcium chloride (anhydrous) was added, while pipetting up and down, and 20 µL of 0.1M spermidine (free base) was added, while pipetting up and down. The tube was placed on a Turbomix™ attachment for a Vortex-Genie® set at 2, and allowed to shake for 10 minutes at room temperature. The tube was removed from the shaker and allowed to settle for 3-5 minutes before being centrifuged for 15 seconds at 5,000 rpm. The supernatant was removed, 250 µL cold ethanol (100%) was added and the tube was finger vortexed to dislodge the pellet and ensure a uniform suspension. The DNA-coated microparticles settled for 3-5 minutes, and the tube was centrifuged again for 15 seconds at 5,000 rpm. The pellet was resuspended in 120 µL cold ethanol (100%), and finger vortexed to ensure dispersal. Macrocarriers were placed into macrocarrier holders, autoclaved for sterility, coated with 10 µL of the prepared solution and allowed to dry completely prior to bombardment.

Bombardment of embryos was done using a PDS-1000™ (Bio-Rad) per manufacturer's specifications at 900 psi under 28 inches vacuum at a distance of 6 cm from the stopping screen. Each sample was bombarded once, and then returned to 50 moles/m²s 24-hour lighting overnight at 28° C. The next day, embryos were transferred to fresh 'resting medium' for 7 days under the same temperature and lighting conditions. Embryos were subsequently transferred to 'sel-5 Bi medium' Cresting medium with the addition of 5 mg/L Bialaphos) for 7 days, transferred a second time to the same medium for 14 days and then transferred to 'pre-regen medium' (MS salts and vitamins, 30 g/L sucrose, 700 mg/L L-proline, 15 mg/L silver nitrate, 500 mg/L MES, 100 mg/L casein hydrolysate, 100 mg/L myo-inositol and 3.3 mg/L dicamba, 2.5 mg/L ABA, 1 mg/L BAP, 0.5 mg/L NAA and 5 mg/L Bialaphos adjusted to pH 5.8 and solidified with 2.3 g/L Gelzan) for 7 days under the same temperature and lighting conditions. Tissues were then transferred to 'regen media' (MS salts and vitamins, 30 g/L sucrose, 100 mg/L myo-insitol and 5 mg/L Bialaphos adjusted to pH 5.8 and solidified with 2.3 g/L Gelzan) under a 16/8 light/dark photoperiod with 90 moles/m²s lighting for 14 days at 28° C. Plantlets were transferred to 'plant robusting medium' (MS salts and vitamins, 30 g/L sucrose, 500 mg/L MES and 100 mg/L myo-insitol adjusted to pH 5.8 and solidified with 2.3 g/L Gelzan) under 150-200 moles/m²s lighting at 28° C. using the same photoperiod. Once plants grew to at least 8 cm, a 2 cm section of leaf tissue was collected on wet ice, and delivered to a 4° C. cold room for analysis. Plantlets were then transplanted into soil and transferred to the greenhouse and analyzed via molecular analysis.

Molecular Analysis Bialophos-Selected Events
Genomic DNA Isolation for qPCR from Callus Tissue Tissue samples were collected in 96-well collection plates (Qiagen) and lyophilized for 48 hours. Tissue disruption was performed with a Kleco™ tissue pulverizer (Garcia Manufacturing, Visalia, Calif.) in Biosprint96 RLT lysis Buffer™ with one stainless steel bead. Following tissue maceration, genomic DNA was isolated in a high throughput format using the Biosprint96 Plant Kit™ (Qiagen) and the Biosprint96 extraction Robot™. Genomic DNA was then diluted to 2 ng/μL.

Copy Number Determination

Gene copy number and the disruption assay were done as described in EXAMPLE 7. Analysis of non-targeted controls and events that are not targeted or disrupted showed a target to reference ratio in the 0.4 to 0.6 range; disrupted or targeted events showed a target to reference ratio in the 0.2 to 0.35 range (FIG. 12).

TABLE 11

Primers and probes for qPCR.

| Name | SEQ ID NO: | Oligo Sequence | Probe (Flourophore/quencher) |
|---|---|---|---|
| MAS604 | 53 | ACACGGCACACACGGCGACATTCA | — |
| MAS606 | 54 | AGGGCAGTGGCCAGTGTTCCTGTG | — |
| UPL69 | — | See Roche | See Roche |
| IVF-Taq | 55 | TGGCGGACGACGACTTGT | — |
| IVR-Taq | 56 | AAAGTTTGGAGGCTGCCGT | — |
| IV-Probe | 57 | CGAGCAGACCGCCGTGTACTTCTACC | HEX/BHQ |
| TQPATS | 62 | ACAAGAGTGGATTGATGATCTAGAGAGGT | — |
| TQPATA | 63 | CTTTGATGCCTATGTGACACGTAAACAGT | — |
| TQPATFQ | 64 | GGTGTTGTGGCTGGTATTGCTTACGCTGG | CY5/BHQ2 |
| ZGP3S | 65 | CCTGCTCCACTACCAGTACAA | — |
| ZGP3A | 66 | GTCCAAGAAGGTGACCTTCTC | — |
| TQZGP3 | 67 | AGATCACCGACTTTGCGCTCTTT | 6FAM/BHQ1 |

Locus-Specific In-Out PCR

Locus-specific in-out PCR was done as described in EXAMPLE 5.

TABLE 12

Primer sequences for in-out PCR.

| Name | SEQ ID NO: | Oligo Sequence |
|---|---|---|
| E32-5F3 | SEQ ID NO: 68 | GAAGGCAAAACGAATATAAGTGCATTCGG |
| E32-OLP-F3 | SEQ ID NO: 69 | TCTACAGTGAACTTTAGGACAGAGCCA |
| E32-OLP-R1 | SEQ ID NO: 70 | TCGTGGATAGCACTTTGGGCT |
| E32-3R2 | SEQ ID NO: 71 | GCCCTTACAGTTCATGGGCG |

Expected amplification sizes for the 5' end amplicon was 1,874 bp and the 3' end was 2,089 bp. The PCR bands were excised and sequenced. The resulting sequence data confirmed that the amplicons contained the expected genomic E32 locus-donor chromosomal junctional sequences.

Southern Blot

DNA from events that showed positive disruption and in-out PCR were analyzed by Southern blots to confirm intact donor insertion at the target. DNA was digested with NcoI and probed with flanking genomic DNA outside the homology arms (FIG. 14). A band at 1,950 bp was predicted for the endogenous, non-targeted locus and a band of 4,370 bp was predicted for a targeted locus.

For Southerns, genomic DNA (from 1 μg to 5 μg) was digested in 1× Buffer 3 (New England BioLabs) with 50 Units of NcoI (New England BioLabs) in a final volume of 125 μL. Samples were incubated at 37° C. overnight. The digested DNA was concentrated by re-precipitation with Quick Precipitation Solution™ (Edge Biosystems) according to manufacturer's suggested protocol. Recovered digest was resuspended in 30 μL of 1× loading buffer and incubated at 65° C. for 30 minutes. Resuspended samples were loaded onto a 0.8% agarose gel prepared in 1×TAE (0.8M Trisacetate [pH8.0]/0.04 mM EDTA) and electrophoresed in 1×TAE buffer. The gel was sequentially subjected to denaturation (0.2 M NaOH/0.6M NaCl) for 30 minutes, and neutralization (0.5 M Tris-HCl [pH7.5]/1.5M NaCl) for 30 minutes. Transfer of DNA fragments was performed by passively wicking 20×SSC solution overnight through the gel onto treated Immobilon NY+™ (Millipore) Following transfer, the membrane was briefly washed with 2×SSC, cross-linked with a StrataLinker 1800™ (Stratagene), and baked at 80° C. for 1 hour.

Blots were incubated with prehybridization solution (Perfect Hyb Plus™, Sigma) for 1 hour at 65° C. in glass roller bottles using a model 400 Hybridization Incubator™ (Robbins Scientific). For probe preparation, genomic sequence outside the donor homology region was PCR amplified with primers (Table 13) and purified from agarose gels using a QIAquick gel extraction Kit™ (Qiagen). The fragment was labeled with 3000 Ci/mmol $\alpha^{32}$P-dCTP (Perkin/Elmer/BLU513H) using Prime-IT® II Random Primer labeling Kit™ (Stratagene) according to manufacturer's suggested protocol. Blots were hybridized overnight at 65° C. with denatured probe at approximately $2\times10^6$ counts per mL/hybridization buffer. Following hybridization, blots were washed at 65° C. with 0.1×SSC/0.1% SDS for 40 minutes.

Blots were exposed using phosphor imager screens (Molecular Dynamics) and imaged using a Storm Imaging System™ (Molecular Dynamics, Storm 860™).

TABLE 13

Primers used to make Southern probe.

| Name | SEQ ID NO: | Oligo Sequence |
|---|---|---|
| MAS600 | SEQ ID NO: 72 | TGTTTATAGAGCCTATTGGATACA |
| MAS603 | SEQ ID NO: 73 | AGTGCATTCGGATTACTGTTTAGTC |

A total of 912 events were screened by disruption and in-out PCR and 16 were confirmed to be targeted based on Southern analysis. The targeting frequency for a donor fragment within the E32 genomic locus was calculated to be 1.8%.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method for integrating one or more exogenous nucleic acid sequences into the genome of a maize cell having an E32 locus, said method comprising the steps of:
   making a double-stranded cleavage in the E32 locus using a site specific zinc finger nuclease, wherein the site specific zinc finger nuclease comprises three or more zinc finger motifs selected from the group consisting of SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, and SEQ ID NO:52; and
   ligating a polynucleotide comprising one or more exogenous nucleic acid sequences into the cleavage using a ligase or a recombinase, wherein the polynucleotide is integrated into the cleavage.

2. The method of claim 1, further comprising the step of expressing a product of the one or more exogenous sequences.

3. The method of claim 1, wherein the one or more exogenous nucleic acid sequences comprise a coding sequence, a regulatory sequence, or a target site for a DNA-binding domain.

4. The method of claim 2, wherein the one or more exogenous nucleic acid sequences comprise a coding sequence, a regulatory sequence, or a target site for a DNA-binding domain.

5. The method of claim 3, wherein the coding sequence encodes for a product that confers: herbicide resistance; herbicide tolerance; insect resistance; insect tolerance; disease resistance; disease tolerance; stress tolerance; stress resistance; a change in oxidative stress; increased yields of oil; a change in food content and makeup; a change in physical appearance; male sterility; drydown; standability; prolificacy; a change in starch quantity or quality; a change in oil quality; a change in protein quality or quantity; a change in amino acid composition or combinations thereof.

6. The method of claim 4, wherein the coding sequence encodes for a product that confers: herbicide resistance; herbicide tolerance; insect resistance; insect tolerance; disease resistance; disease tolerance; stress tolerance; stress resistance; a change in oxidative stress; increased yields of oil; a change in food content and makeup; a change in physical appearance; male sterility; drydown; standability; prolificacy; a change in starch quantity or quality; a change in oil quality; a change in protein quality or quantity; a change in amino acid composition or combinations thereof.

7. The method of claim 2 wherein the exogenous sequence is chose from the group consisting of the phosphinothricin-N-acetyl-transferase (PAT) gene and the aryloxyalkanoate dioxygenase (AAD-1).

8. The method of claim 1, wherein the polynucleotide further comprises nucleotide sequences that are homologous to sequences in the E32 locus.

9. The method according to claim 8, wherein the homologous nucleotide sequences flank the exogenous sequence.

10. The method of claim 1, wherein the polynucleotide further comprises a promoter.

11. The method of claim 1, wherein one or more of the integrated exogenous nucleic acid sequences are transmitted to progeny in subsequent generations.

12. A maize plant or maize plant part comprising a maize cell having an E32 locus, wherein the genome of the maize cell comprises one or more nucleic acid exogenous sequences, wherein the one or more nucleic acid exogenous sequences are integrated into the genome of the maize cell within the E32 locus according to the method of claim 1.

13. A maize seed comprising a maize cell having an E32 locus, wherein the genome of the maize cell comprises one or more nucleic acid exogenous sequences, wherein the one or more nucleic acid exogenous sequences are integrated into the genome of the maize cell within the E32 locus according to the method of claim 1.

* * * * *